(12) United States Patent
Lohrmann et al.

(10) Patent No.: US 7,977,403 B2
(45) Date of Patent: Jul. 12, 2011

(54) ANTISEPTIC CONTAINING SILICONE ELASTOMERS

(75) Inventors: Marc Lohrmann, Böblingen (DE);
Heinz Pudleiner, Krefeld (DE);
Joachim Hyner, Langenfeld (DE)

(73) Assignee: Bayer Innovation GmbH, Dusseldorf (DE)

( * ) Notice: Subject to any disclaimer, the term of this patent is extended or adjusted under 35 U.S.C. 154(b) by 556 days.

(21) Appl. No.: 11/741,275

(22) Filed: Apr. 27, 2007

(65) Prior Publication Data

US 2007/0255004 A1 Nov. 1, 2007

(30) Foreign Application Priority Data

Apr. 28, 2006 (DE) .................. 10 2006 020 644

(51) Int. Cl.
*A61F 2/02* (2006.01)
(52) U.S. Cl. ........ 523/112; 523/113; 514/642; 514/635; 514/659; 424/423; 524/588
(58) Field of Classification Search .................. 524/858, 524/860–862, 588; 514/556, 634–635, 642; 514/659; 604/508; 424/423; 523/112, 113
See application file for complete search history.

(56) References Cited

U.S. PATENT DOCUMENTS

| | | | |
|---|---|---|---|
| 2,541,137 A | | 2/1951 | Warrick |
| 3,002,951 A | | 10/1961 | Johannson |
| 3,428,576 A | | 2/1969 | Dickinson |
| 3,715,334 A | | 2/1973 | Karstedt |
| 4,107,313 A | | 8/1978 | Bailey |
| 4,230,686 A | | 10/1980 | Schopflin |
| 4,714,563 A | * | 12/1987 | Kajs et al. ..................... 510/133 |
| 4,925,686 A | * | 5/1990 | Kastin ........................... 426/131 |
| 5,165,952 A | * | 11/1992 | Solomon et al. ............. 427/2.25 |
| 5,338,312 A | * | 8/1994 | Montgomery ................ 604/230 |
| 5,439,685 A | * | 8/1995 | Augros ......................... 424/430 |
| 5,466,726 A | | 11/1995 | Inoue |
| 5,616,338 A | * | 4/1997 | Fox et al. ...................... 424/423 |
| 6,150,489 A | | 11/2000 | Pudleiner |
| 6,455,059 B1 | | 9/2002 | Albers |
| 6,558,686 B1 | * | 5/2003 | Darouiche .................... 424/423 |
| 6,605,069 B1 | | 8/2003 | Albers |
| 6,723,333 B1 | | 4/2004 | Albers |
| 7,381,751 B2 | * | 6/2008 | Sarangapani .............. 514/772.3 |
| 7,648,487 B2 | * | 1/2010 | Ito et al. ........................ 604/230 |
| 2009/0076480 A1 | * | 3/2009 | Pudleiner et al. ............. 604/508 |

FOREIGN PATENT DOCUMENTS

| | | | |
|---|---|---|---|
| CA | 2155564 | | 12/1996 |
| DE | 10 2004 054 040 | * | 5/2010 |
| EP | 0057098 | | 4/1985 |
| EP | 393 511 | * | 10/1990 |
| EP | 0328421 | | 4/1993 |
| EP | 688 564 | * | 12/1995 |
| EP | 0688564 | | 8/1999 |
| GB | 702268 | | 1/1954 |
| WO | 99/32168 | * | 7/1999 |
| WO | WO2006050806 | * | 10/2005 |

OTHER PUBLICATIONS

International Search Report for PCT/EP2007/003344, mailed Jan. 14, 2008.
European Committee for Standardization, "Biological Evaluation of Medical Devices, Part 5: Tests for In Vitro Cytotoxicity", European Standard, May 1999, Doc. EN ISO 10993-5, pp. 1-12.
Brunauer, "Adsorption of Gases in Multimolecular Layers", Journal of the American Chemical Society, vol. 60, pp. 309-319, Feb. 1938.
Liedl, "Katheterassoziierte Harnwegsinfektionen" in Urogenitale Infektionen, Ed. A. Hofstetter, Springer, pp. 241-164 (1999).

* cited by examiner

*Primary Examiner* — Margaret G Moore
(74) *Attorney, Agent, or Firm* — Baker Donelson Bearman, Caldwell & Berkowitz, PC

(57) ABSTRACT

The present invention relates to compositions comprising silicone elastomers and antiseptics in homogeneous distribution, to processes for the preparation thereof and to uses thereof, for example, in medical articles.

20 Claims, 6 Drawing Sheets

ANTISEPTIC CONTAINING SILICONE ELASTOMERS

CROSS REFERENCE TO RELATED APPLICATIONS

This application claims priority to DE10 2006 020 644.4 filed Apr. 28, 2006, the content of which is incorporated by reference of its entirety.

BACKGROUND OF THE INVENTION

1. Field of the Invention

The invention relates to compositions comprising silicone elastomers and antiseptics in homogeneous distribution, to a process for the preparation thereof and to the use thereof in medical articles.

2. Description of Related Art

Medical articles made of plastics (e.g. catheters) are currently used in a large number of applications for diagnostic and therapeutic purposes. Central venous catheters are used for example in modern intensive care for invasive monitoring and treatment strategies such as continuous haemofiltration. Urinary tract catheters are an essential component of modern medical care and are indispensable, for example in the treatment of impairments of the flow of urine. Although modern medical articles have substantially improved the treatment of intensive-care patients, their application is associated with considerable risks. The frequent use of plastics articles such as, for example, catheters has led to a drastic increase in so-called polymer-associated infections. Polymer-associated infections are in general mainly caused by multiresistant nosocomial pathogens which adhere to an article's plastic surface and then colonize it (Urogenitale Infektionen, Ed. A. Hofstetter, Springer 1999, 241-64).

Catheter-associated infections currently represent an important cause of morbidity and mortality of intensive-care patients. Recent studies demonstrate that 70 to 90% of nosocomially acquired urinary tract infections are associated with an instrumentation (catheterization) of the urinary tract. A single catheterization of the urinary bladder is followed by bacteriuria for example in 0.5 to 28% of patients. The incidence of catheter-associated urinary tract infections moreover depends on the catheter time and the age, sex and condition (immunocompetence) of the patient (Urogenitale Infektionen, Ed. A. Hofstetter, Springer 1999, 241-64). However, the use of catheters not only involves a higher risk of infection for the patients, but also causes high follow-up therapy costs. Givens and Wenzel were able to show that nosocomial urinary tract infections increase the postoperative inpatient stay by an average of 2.4 days and cause corresponding additional costs (I Urol. 1980, 124: 646-48). Prevention of catheter-associated infections therefore has the highest priority in modem medicine for both medical and economic reasons.

Catheter-associated infections, possibly developing into sepsis, are, besides traumatic and thromboembolic complications, a serious problem on use of central venous catheters in intensive care.

Numerous studies have revealed that coagulase-negative staphylococci, the transient organism *Staphylococcus aureus* and various *Candida* species are the main causes of catheter-associated infections. During application of the catheter, these microorganisms, which are ubiquitously present on the skin, penetrate the physiological barrier of the skin and thus reach the subcutaneous region and eventually the bloodstream. Adhesion of the bacteria to the plastic surface is regarded as an essential step in the pathogenesis of foreign-body infections. Adhesion of the cutaneous organisms to the polymer surface is followed by the start of metabolically active proliferation of the bacteria with colonization of the polymer. This is associated with production of a biofilm through bacterial excretion of extracellular glycocalix. The biofilm assists adhesion of the pathogens and protects them from attack by certain cells of the immune system. In addition, the film forms a barrier which is impenetrable by many antibiotics. Extensive proliferation of the pathogenic organisms on the polymer surface may finally be followed by septic bacteriaemia. Therapy of such infections requires removal of the infected catheter because chemotherapy with antibiotics would require unphysiologically high doses.

The incidence of bacterially induced infections with central venous catheters averages about 5%. Overall, central venous catheters prove to be responsible for about 90% of all cases of sepsis in intensive care. The use of central venous catheters therefore not only involves a higher risk of infection for the patients, but also causes extremely high follow-up therapy costs (subsequent treatment, extended stays in the clinic).

The problems associated with urinary tract and central venous catheters can be solved only in part by prophylactic measures such as, for example, hygienic measures (handling of the catheters, training of the staff) or routine endoluminal antibiotic administrations.

A rational strategy for preventing polymer-associated infections consists of modifying the polymeric materials used. The aim of this modification must be to inhibit bacterial adhesion and the proliferation of already adherent bacteria, for causal prevention of foreign-body infections in this way. This can be achieved, for example, by incorporating a suitable antimicrobially active substance into the polymer matrix (e.g. antibiotics), provided that the incorporated active ingredient can also diffuse out of the polymer matrix in a controlled manner. An infection-resistant material ought therefore to have the following properties:

1) wide range of effects against the microorganisms relevant for infections associated with the appropriate catheter, especially coagulase-negative staphylococci such as *Staphylococcus aureus* for central venous catheters and enterococcal, *Proteus, Klebsiella, Enterobacter* species with urethral catheters;

2) sufficient duration of the antimicrobial effect, the requirement being for durations of action of longer than 30 days;

3) protection of the internal and external surfaces of the materials; and 4) polymer modification must not impair either the biocompatibility (thromogenicity, cytotoxicity) or the mechanical properties (tensile strength, modulus, hardness) of the material.

Methods for producing antimicrobially modified polymers for medical applications have already been disclosed.

EP-A 0 696 604 describes aliphatic thermoplastic polyurethane-ureas which are hydrophilic owing to the inclusion of urea groups but are unable to prevent bacterial adhesion and proliferation on the catheter surface. EP-A 1 067 974, EP-A 0 927 222, EP-A 1 128 724 and EP-A 1 128 723 describe antibacterially effective thermoplastic compounds into which the active ingredients are introduced in sufficiently fine and homogeneous distribution by high viscosity processing techniques. Comparative experiments have shown that the shear forces in the extruder are, however, insufficient to achieve the required distribution of the powdered active ingredients in the silicone solid-phase rubbers employed for producing catheter tubings.

Polymer materials for medical applications which have active ingredient-containing coatings are also mentioned in EP-A 328 421. Descriptions are given of processes for producing the antimicrobially active coatings and methods for application onto the surfaces of medical devices. The coatings consist of a polymer matrix, in particular of polyurethanes, silicones or biodegradable polymers, and of an antimicrobially active substance, preferably of a synergistic combination of a silver salt (silver sulphathiazine) with chlorhexidine or an antibiotic. This publication describes combinations of various polymers, inter alia, also silicones, with antibiotics. However, the difficulties of incorporating powdered active ingredients into silicone rubbers are not dealt with. The process according to the invention is not described in this publication.

European patent EP-A 0 688 564 describes active ingredient-containing silicone elastomers whose delivery rate can be controlled by the density of crosslinking. The special significance of the particle size of active ingredients in silicone elastomers and how this is achieved is not mentioned. In addition, additives which assist the release of active ingredients are described but are deliberately dispensed with in the present invention.

U.S. Pat. No. 4,230,686 (Schopflin et al) describes room temperature-crosslinking (RTV) silicone elastomers which comprise non-ionic lipophilic active ingredients. According to this publication (column 5, lines 57 to 59), such silicone elastomers are suitable as active ingredient carriers with slow release only for lipophilic non-ionic active ingredients. In addition, column 7, lines 51 to 60, describe the incorporation of the active ingredients as dry powders into the silicone elastomers. The particle size is said in this case to be chosen in such a way that as the solubility of the active ingredient in water increases the size of the incorporated particles (4 to 400 μm) must be larger.

SUMMARY OF THE INVENTION

It was an object of the instant invention to provide novel silicone elastomers which are suitable for producing medical shaped articles such as for short-term implants, especially catheters, and efficiently prevent surface colonization by microorganisms for a prolonged period (more than 30 days).

An additional object of the instant invention was to provide a process that makes it possible to incorporate active ingredients in fine distribution into silicone elastomers.

It has now surprisingly been found that silicone elastomers according to the present invention which comprise antiseptics, especially those selected from the group of bispyridinium alkanes, of polymeric amidobiguanides, of quaternary ammonium compounds, in particular benzalkonium chloride, and chlorhexidine, taurolidine and triclosan, with a very small particle size (about 3 μm), when used in medical shaped articles provide very good activity against bacterial colonization on surfaces of such articles over several weeks.

The present invention therefore relates to silicone elastomers comprising at least one antiseptic in homogeneous distribution, where the antiseptic, in particular in the form of a suspension, advantageously has an average particle size $d_{50}$ of from 0.5 to 15 μm, preferably between 1 and 10 μm, and preferably has a particle size distribution between 0.1 to 30 μm, particularly preferably 0.5 to 20 μm.

The present invention further relates to suspension for incorporating an antiseptic into a silicone-rubber formulation, it being possible in a preferred embodiment, for the suspending medium to be chemically incorporated into the silicone elastomer.

The present invention further relates to shaped articles which are produced by crosslinking silicone-rubber formulations according to the invention.

The present invention additionally relates to the use of the silicone elastomers according to the invention for producing medical tubings, urinary bladder catheters (Foley catheters, intermittent catheters, suprapubic and transurethral catheters), haemodialysis catheters, single- and multiple-lumen central venous catheters, peripheral catheters, thermodilution catheters, and/or balloon catheters for percutaneous transluminal coronary angioplasty (PTCA), or the like.

The present invention further relates to medical appliances, especially catheters, which can be produced from silicone elastomers according to the instant invention.

The present invention further relates to a process for preparing silicone rubbers comprising polymerizine of a silicone-rubber formulation as described herein. The present invention further relates to a silicone-rubber formulation per se.

Additional objects, features and advantages of the invention will be set forth in the description which follows, and in part, will be obvious from the description, or may be learned by practice of the invention. The objects, features and advantages of the invention may be realized and obtained by means of the instrumentalities and combinations particularly pointed out in the appended claims.

The accompanying drawings, which are incorporated in and constitute apart of the specification, illustrate particular embodiments of the invention, and, together with the general description given above and the detailed description of certain embodiments given below, serve to explain the principles of the invention.

Figure 9:
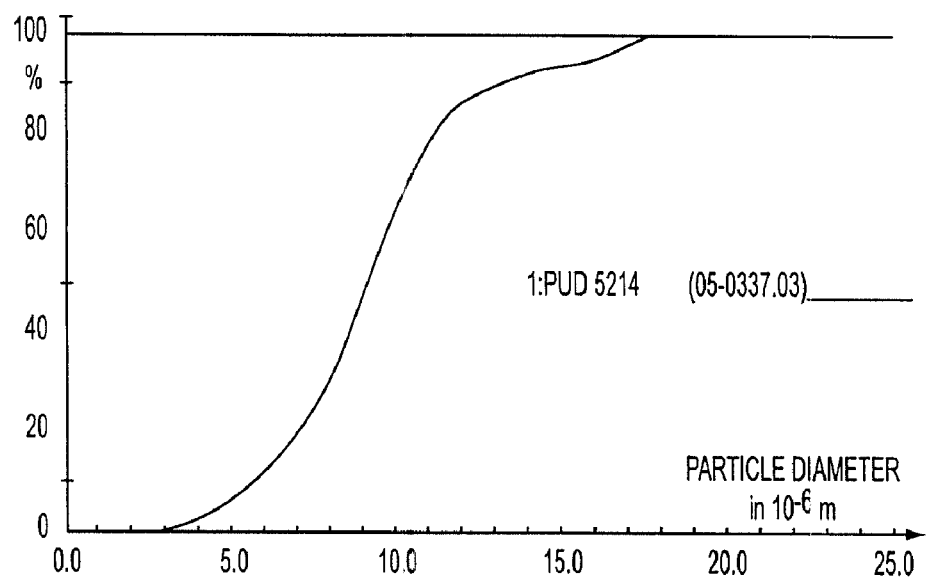

FIG. 9 demonstrates ultracentrifuge particle size distribution of the PHMB suspension from Example 2.

Figure 10:
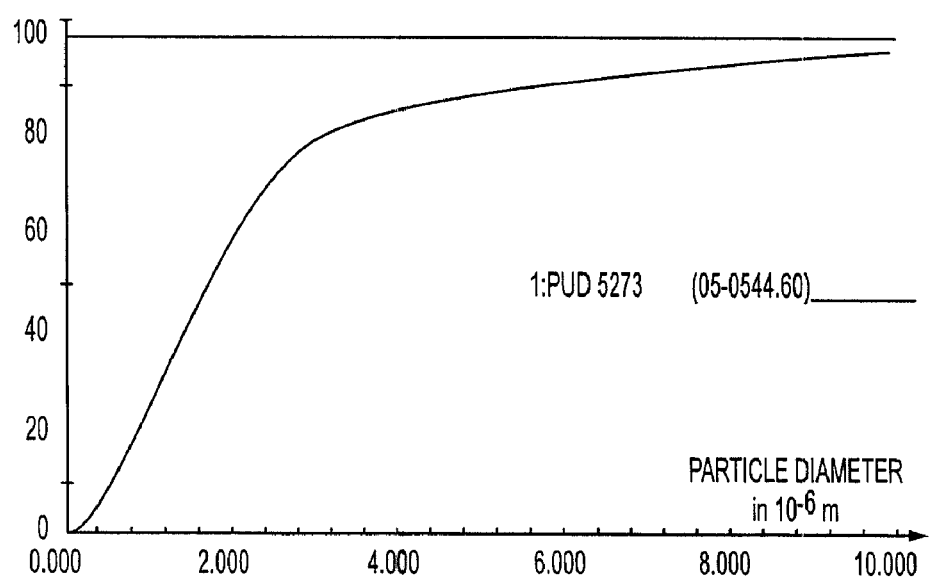

FIG. 10 demonstrates ultracentrifuge particle size distribution of the octenidine dihydrochloride suspension from Example 1.

Figure 11:
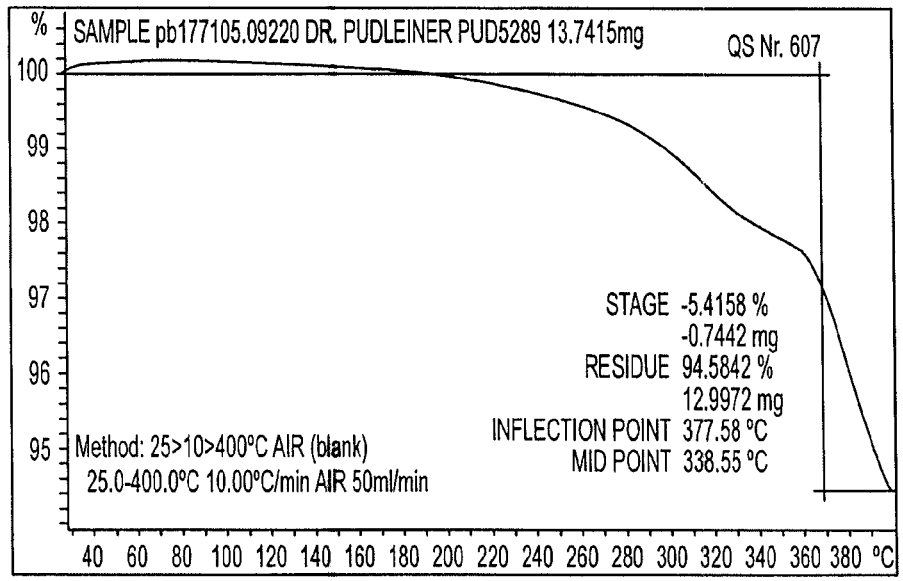

FIG. 11 demonstrates TGA curve of the suspension from Example 1.

Figure 12:
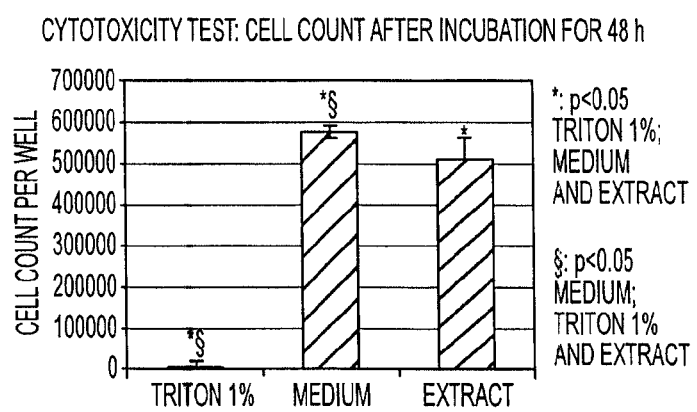

FIG. 12 demonstrates cell count as measured in Example 15.

Figure 13:
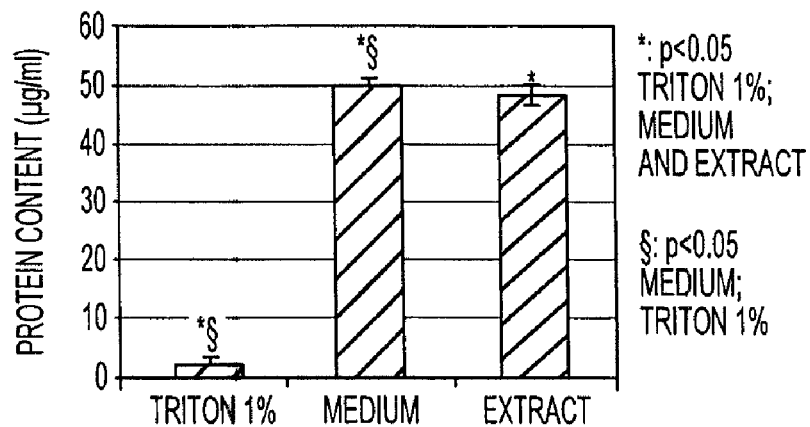

FIG. 13 demonstrates protein content of the cells as measured in Example 15.

Figure 14:
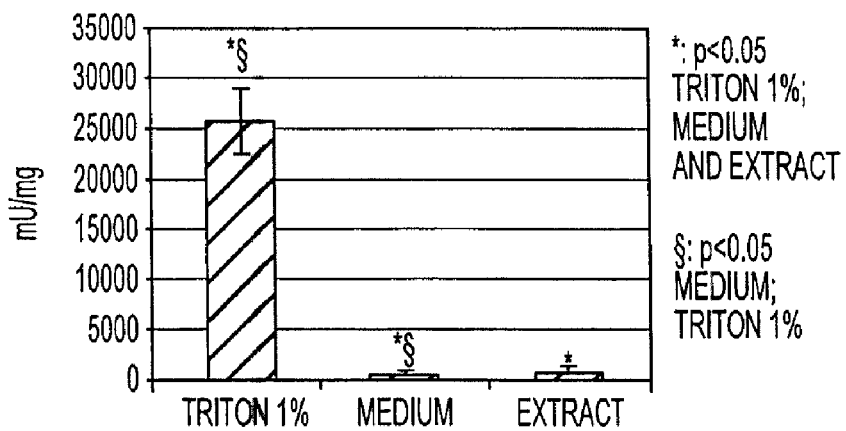

FIG. 14 demonstrates LDH activity as measured in Example 15.

DETAILED DESCRIPTION OF A PREFERRED EMBODIMENT

A silicone-rubber formulation according to the invention preferably comprises the following components:

A) at least one polysiloxane of formula (I)

wherein
R¹ and R² may in each case be identical or different, and are each $C_1$-$C_{12}$-alkyl, $C_1$-$C_{12}$-fluoroalkyl, and optionally substituted phenyl or naphthyl, R³ and R⁴ may in each case be identical or different, expressly including each repeating unit, and are each $C_1$-$C_{12}$-alkyl, $C_1$-$C_{12}$-fluoroalkyl and optionally substituted phenyl or naphthyl, and additionally —OSiR²R³R, in which R symbolizes the continuation of the siloxane chain in analogy to formula (I) in the branching so that the polysiloxane molecule may have branching units of the formula $SiO_{4/2}$ and $R^3SiO_{3/2}$, R¹ and R³ are additionally independently of one another $C_1$-$C_{12}$-alkenyl, in which case the polysiloxane comprises from 0.0002 to 3% by weight of vinyl groups, and the molecule has at least two olefinically unsaturated multiple bonds, x is an integer from 2 to 15 000 and can be varied so that the viscosity of the polysiloxane extends from 0.1 to 1000 Pas at 25° C., B) optionally at least one filler having a BET specific surface area of from 50-500 m²/g,
C) optionally at least one filler having a BET specific surface area of not more than 50 m²/g,
D) optionally at least one auxiliary,
E) optionally at least one saturated water repellent selected from the group consisting of disilazanes, siloxanediols, alkoxysilanes, silylamines, silanols, acetoxysiloxanes, acetoxysilanes, chlorosilanes, chlorosiloxanes and alkoxysiloxanes,
F) optionally at least one unsaturated water repellent selected from the group consisting of multiply vinyl-substituted methyldisilazanes, and methylsilanols and alkoxysilanes each having unsaturated radicals selected from the group consisting of alkenyl, alkenylaryl, acryl and methacryl,
G) optionally at least one nonfunctional polysiloxane,
H) optionally at least one inhibitor for hydrosilylation reaction,
I) at least one polyhydrosiloxane of formula (II)

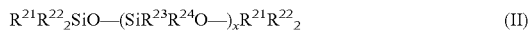

$$R^{21}R^{22}_2SiO-(SiR^{23}R^{24}O-)_xR^{21}R^{22}_2 \qquad (II)$$

wherein
R²¹ and R²² may in each case be identical or different, and are each $C_1$-$C_{12}$ alkyl, $C_1$-$C_{12}$-fluoroalkyl, and optionally substituted phenyl or naphthyl, R²³ in each case expressly including each repeating unit independently of one another is hydrogen, $C_1$-$C_{12}$-alkyl, $C_1$-$C_{12}$-fluoroalkyl and optionally substituted phenyl or naphthyl, additionally —OSiR²³R²⁴R in which R symbolizes the continuation of the siloxane chain in analogy to formula (II) in the branching so that the polyhydrosiloxane molecule may have branching units of the formula $SiO_{4/2}$ and $R^{23}SiO_{3/2}$, where R²³ in at least 4 of these silyldioxyl units is hydrogen so that a molecule has at least 4 crosslinking sites, R²⁴ in each case expressly including each repeating unit independently of one another is $C_1$-$C_{12}$-alkyl, $C_1$-$C_{12}$-fluoroalkyl and optionally substituted phenyl or naphthyl, additionally —OSiR²³R²⁴R in which R symbolizes the continuation of the siloxane chain in analogy to formula (II) in the branching so that the polyhydrosiloxane molecule may have branching units of the formula $SiO_{4/2}$ and $R^{23}SiO_{3/2}$, x is an integer from 4 to 10 000 and cam be varied so that the viscosity of the polymer extends from 0.0005 to 0.1 Pas at 25° C., J) at least one catalyst comprising at least one element of the platinum group, where up to a maximum of 3 parts by weight of metal compounds such as oxides and/or carbonates, and further salts and complex compounds, of Fe, Al, Zn, Ti, Zr, Ce or other lanthanoids can be present based on 100 parts by weight of component A), K) at least one suspension, comprising a suspending medium of polysiloxanes of the formula (I) and/or (II) and/or nonfunctional siloxanes G), and at least one antiseptic, in particular those selected from the group of bispyridinium alkanes, of polymeric amidobiguanides, of quaternary ammonium compounds, in particular benzalkonium chloride, and chlorhexidine, taurolidine and triclosan.

Bispyridinium Alkanes

Active ingredients suitable in principle in the present invention include all the active ingredients defined in claims 1 to 4 on page 28 of DE 27 08 331 C2 the content of which s incorporated herein by reference. The compounds from Examples 1-82 (page 5 to page 18, line 19) are preferably employed, and octenidine, its hydrochloride or very particularly preferably the dihydrochloride 1,1'-(1,10-decanediyl) bis[4-(octylamino)pyridinium]dichloride are particularly preferably employed.

These active ingredients referred to as bis[4-(substituted amino)-1-pyridinium]alkanes are defined by the general formulae (III) and (IV)

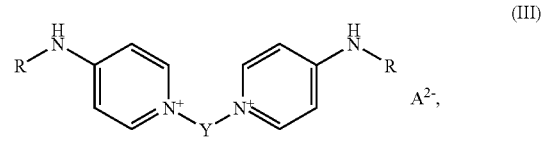

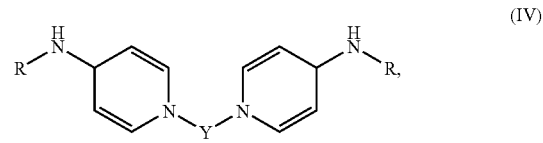

in which
Y is an alkylene group having 4 to 18 carbon atoms,
R is $C_6$-$C_{18}$-alkyl, $C_5$-$C_7$-cycloalkyl or phenyl which is substituted by a halogen atom, and
A is two monovalent or one divalent anion.
Y is preferably 1,10-decylene or 1,12-dodecylene, particularly preferably 1,2-dodecylene.
R is preferably n-hexyl, n-heptyl or n-octyl, particularly preferably n-octyl.
A is for example one sulphate, in each case 2 fluoride, chloride, bromide, iodide, or methanesulphonate ions, preferably in each case 2 fluoride, chloride, bromide, particularly preferably 2 chloride ions.

Formula (IV) designates the corresponding free bases which can be prepared by neutralization from the salts of the formula (III) by conventional methods of organic chemistry. The salts of the formula (III) can be frequently depicted in the literature also in the form of the formula (V)

$$\text{formula (IV)} \times H_2A \qquad (V)$$

in which "formula (IV)" and A have the meanings indicated above. By its nature, a chemical formula is only a simplified depiction of reality. In this case, tautomers are involved, for which there is no evidence that they can be distinguished under usual conditions and temperatures. For octenidine dihydrochloride there are nevertheless in each case 2 chemical abstracts registry numbers and 2 numbers in the European inventory of existing commercial chemical substances. It is not intended to be relevant to the present invention whether compounds of the formula (III) or of the formula (V) are employed, and/or in which form they are present in the polymer composition. Salts of the formula (III) or (V) are preferably employed.

Polymeric Amidobiguanide

Suitable aminopropylbiguanides that can be used according to the instant invention can include those of formula VI

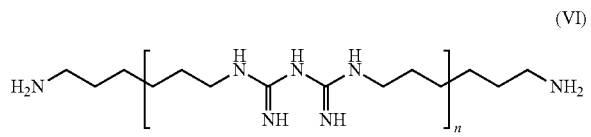

wherein n is an integer between 1 and 500. It is also possible to use salts of compounds of the formula VI.

The compounds of the formula VI are known. Their preparation is described for example in GB 702 268 and GB 1 152 243 which are incorporated herein by reference in their entirety. In addition, these compounds are also commercially available, e.g. as Vantocil™, Cosmocil™ or as Arlagard™ E from ICI Chemicals.

The compounds of the formula VI may, depending on their mode of preparation, comprise certain proportions of a by-product of the formula VII

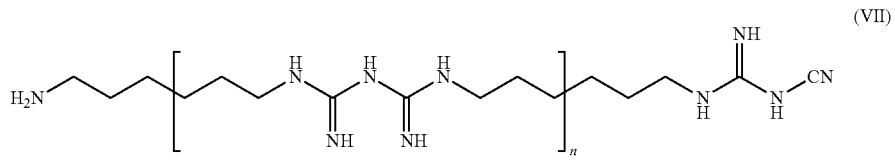

or salts thereof, in which n is likewise an integer between 1 and 500. Mixtures of compounds of the formula VI with those of the formula VII can likewise be used according to the present invention. The proportion of compounds of the formula VII based on the total amount of compounds of the formula VI and compounds of the formula VII is preferably less than 20 percent by weight, more preferably less than 2 to 10 percent by weight and is particularly preferably zero percent by weight.

The index n in the formulae VI and VII is preferably from 1 to 200, more preferably 2 to 100, particularly preferably 2 to 50 and very particularly preferably 3 to 12. Depending on the meaning of the index n in the formulae VI or VII, the molecular weight of the aminopropylbiguanides which can be used can be as low as the molecular weight of the monomers of the formula VI (n=1), or in the range from about 600 to 1600 if oligomers are used, i.e. if n is for example 3 to 8, or else in the range from about 50 000 to about 90 000 if n stands for distinctly higher values, e.g. for about 270 to 500.

Suitable salts include those with inorganic or organic acids, for example hydrochlorides, hydrobromides, borates, acetates, gluconates, sulphonates, maleates, ascorbates, tartrates or citrates.

The antiseptics are preferably incorporated into the silicone-rubber formulations according to the present invention in a concentration appropriate for their antimicrobial activity. The antiseptics are preferably normally used in a concentration range from 0.01 to 10.0% by weight, advantageously from 0.05 to 5% by weight, particularly preferably 0.1 to 5% by weight, in the silicone elastomers.

For the purposes of the present invention, component A) is defined by at least one linear or branched polysiloxane of the general formula (I) indicated hereinbefore.

$R^1$ and $R^2$ may in each case be identical or different, and each is preferably $C_1$-$C_{12}$-alkyl, $C_1$-$C_{12}$-fluoroalkyl, and phenyl or naphthyl which is optionally mono- or polysubstituted by F, Cl, $CF_3$, $C_1$-$C_6$-alkyl, $C_1$-$C_6$-alkoxy, $C_3$-$C_7$-cycloalkyl, $C_2$-$C_6$-alkenyl or phenyl.

$R^3$ and $R^4$ may in each case be identical or different, expressly including each repeating unit, and are each preferably $C_1$-$C_{12}$-alkyl, $C_1$-$C_{12}$-fluoroalkyl and phenyl or naphthyl which is optionally mono- or polysubstituted by F, Cl, $CF_3$, $C_1$-$C_6$-alkyl, $C_1$-$C_6$-alkoxy, $C_3$-$C_7$-cycloalkyl, $C_2$-$C_6$-alkenyl or phenyl.

$R^1$ and $R^3$ are preferably in addition independently of one another also $C_1$-$C_{12}$-alkenyl, where the polymer comprises from 0.0002 to 3% by weight of vinyl groups, and each molecule has at least two olefinically unsaturated multiple bonds.

x is preferably an integer from 2 to 15 000 and is varied so that the viscosity of the polymer extends from 0.1 to 1000 Pas at 25° C.

$R^2$ to $R^4$ are particularly preferably $C_1$-$C_{12}$-alkyl.

$R^1$ is particularly preferably vinyl.

$R^2$ to $R^4$ are very particularly preferably methyl.

The viscosity of component A) is preferably between 0.1 and 30 000 Pas.

For the purposes of the present invention, component B) is preferably a filler having a BET specific surface area of between 50 and 500 m²/g. It is expedient for the filler employed to be reinforcing fillers. Reinforcing means in this connection that the mechanical strength properties are improved, in particular tensile strength, and/or tear propagation resistance, etc. are improved. The reinforcing fillers are expediently added in a form which positively influences or at least does not impair the electrical properties of the cured mixtures according to the present invention. This can be achieved, for example, by addition of precipitated or pyrogenic, preferably pyrogenic, silica having a BET surface area of from 50 to 500 m²/g (the BET surface area is determined by the method of S. Brunauer, P. H. Emmett, E. Teller. I Am. Soc. 60, 309 (1938)) which is incorporated herein by reference in its entirety.

The fillers may be hydrophobic or hydrophilic fillers. The fillers B) may be surface-modified, i.e. made water-repellent, e.g. with organosilicon compounds. The modification can take place before and/or during compounding for the silicone-rubber formulation according to the present invention.

Components E) and/or F) are preferably used for making the formulation water-repellent, if desired, with addition of water. Saturated or unsaturated disilazanes and methylsilanols, which may where appropriate also be produced from the disilazanes, in accordance with the definition of components E) or F) are preferably used for rendering the formulation water-repellent.

Preferred ranges for the BET surface area of the filler B) are from 50 to 400, particularly preferably 150 to 300, m²/g. The amount of component B) is expediently between 0 and 75 parts by weight per 100 parts by weight of component A), preferably 20 to 50 parts by weight.

For the purposes of the present invention, component C) is preferably a filler having a BET specific surface area of below 50, more preferably below 40, more preferably below 30, m²/g. So-called "non-reinforcing fillers" which do not improve the mechanical properties, in particular the tensile strength, tear propagation resistance, etc., are expedient. Preference is given to diatomaceous earths, finely ground quartz or cristobalite, other amorphous silicas or silicates. The amount of component C) is expediently between 0 and 300 parts by weight per 100 parts by weight of component A), preferably 0 to 50 parts by weight.

For the purposes of the present invention, the term "auxiliary" according to component D) expediently includes pigments, release agents, extrusion aids, hot-air stabilizers, i.e. stabilizers against hot-air ageing, and the like. The release agents are expediently selected from the group of mould release agents such as, for example, stearyl derivatives or waxes, metal salts of fatty acids. Extrusion agents are, for example, boric acid or PTFE pastes. Hot stabilizers are, for example, metal compounds such as oxides and/or carbonates, and further salts and complex compounds, of Fe, Al, Zn, Ti, Zr, Ce or other lanthanoids and antioxidants. The amount of component D) is expediently between 0 and 10 parts by weight per 100 parts by weight of component A), excluding the presence of more than 3 parts by weight, preferably more than 2 parts by weight, of metal compounds, such as oxides and/or carbonates, and further salts and complex compounds, of Fe, Al, Zn, Ti, Zr, Ce or other lanthanoids.

A silicone-rubber formulation according to the present invention preferably comprises no metal compounds such as oxides and/or carbonates and no further salts and complex compounds of Fe, Al, Zn, Ti, Zr, Ce or other lanthanoids.

For the purposes of the present invention, component E) is a saturated water repellent selected from the group consisting of disilazanes, siloxanediols, alkoxysilanes, silylamines, silanols, acetoxysiloxanes, acetoxysilanes, chlorosilanes, chlorosiloxanes and alkoxysiloxanes. Component E) serves to make the fillers C) and preferably B) water-repellent. Rendering the formulations water-repellent can moreover take place separately before the compounding or in situ during the compounding. The amount of component E) is expediently from 0 to 30 parts by weight, preferably 2 to 25, based on 100 parts by weight of B).

For the purposes of the present invention, component F) is a unsaturated water repellent selected from the group consisting of multiply vinyl-substituted methyldisilazanes, and methylsilanols and alkoxysilanes each having unsaturated radicals selected from the group consisting of alkenyl, alkenylaryl, acryl and methacryl. Component F) likewise serves to make the fillers B) and C) water-repellent. The amount of component F) is expediently from 0 to 2 parts by weight, preferably 0.01 to 1, based on 100 parts by weight of A).

The total amount of components B) and F) is preferably 5-25% by weight based on the total amount of components B) and C), preferably based on B).

For the purposes of the present invention, the term "non-functional polysiloxanes" according to component G) expediently means low molecular weight polysiloxanes which are non-functional in relation to the hydrosilylation reaction, are non-crosslinkable, are preferably trimethylsilyl end-blocked and have dimethyl-, diphenyl or phenylsilyloxy groups with degrees of polymerization of 4-1000, or which reliably make the surface of the insulators water-repellent after crosslinking to give the shaped article, as described for example in EP-A 0 057 098, which is incorporated herein by reference in its entirety. The amount of component G) is expediently from 0 to 15, preferably 1 to 3, parts by weight based on 100 parts by weight of A).

For the purposes of the present invention, the term "inhibitor for the hydrosilylation reaction" according to component H) includes inhibitors known in the art for hydrosilylation reactions with metals of the Pt group, such as, for example, maleic acid and its derivatives, amines, azoles, alkylisocyanurates, phosphines, phosphites and acetylenically unsaturated alcohols in which the OH group is bonded to a carbon atom adjacent to the C—C triple bond, as are described in detail for example in U.S. Pat. No. 3,445,420, which is incorporated herein by reference in its entirety. Component G) is preferably 2-methyl-3-butyn-2-ol or 1-ethynylcyclohexanol or (±)-3-phenyl-1-butyn-3-ol. Component H) is preferably used in a proportionate amount of from 0 to 1 parts by weight based on 100 parts by weight of the total of A) to I). Component H) is preferably present in a proportionate amount of from 0.0001% to 2% by weight, particularly preferably 0.01% by weight to 2% by weight and very particularly preferably 0.05% by weight to 0.5% by weight, in each case based on the total weight of the mixture.

For the purposes of the present invention, component I) is defined by at least one polyhydrosiloxane which has at least two hydrogen atoms directly linked to different silicon atoms, according to the general formula (II) indicated hereinbefore. The following definitions apply to the radicals therein:

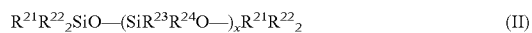

$R^{21}$ and $R^{22}$ may in each case be identical or different, and are preferably each $C_1$-$C_{12}$-alkyl, $C_1$-$C_{12}$-fluoroalkyl, and optionally substituted phenyl or naphthyl.

$R^{23}$ is preferably in each case expressly including each repeating unit independently of one another hydrogen, $C_1$-$C_{12}$-alkyl, $C_1$-$C_{12}$-fluoroalkyl and optionally substituted phenyl or naphthyl, where $R^{23}$ is hydrogen in at least 4 of these silyldioxyl units so that a molecule has at least 4 crosslinking sites.

$R^{24}$ is in each case expressly including each repeating unit independently of one another $C_1$-$C_{12}$-alkyl, $C_1$-$C_{12}$-fluoroalkyl and optionally substituted phenyl or naphthyl.

x is preferably an integer from 4 to 10 000 and is varied so that the viscosity of the polymer extends from 0.0005 to 0.1 Pas at 25° C.

The molar proportion of hydrogen atoms directly linked to a silicon atom in component I) is preferably from 0.01 to 10 mmol/g, particularly preferably from 0.5 to 9 mmol/g and very particularly preferably from 1 to 7, mmol/g.

The amount of component I) is preferably from 0.2 to 30, preferably 0.2 to 20, parts by weight based on 100 parts by weight of component A).

Component J) is a catalyst at least comprising one element of the platinum group.

Component J) is preferably a catalyst which is capable of catalyzing a hydrosilylation reaction and is selected from metals of the platinum group such as Pt, Rh, Ni, Ru and compounds of metals of the platinum group, such as salts or complex compounds thereof. It is further preferred for component J) to be a catalyst comprising an element from the platinum group selected from platinum and platinum compounds, which may optionally be adsorbed on a support, and other compounds of elements of the platinum group. Platinum and platinum compounds are most preferred. Thus, Pt salts, Pt complex compounds with nitrogen, phosphorus compounds and/or alkene compounds or Pt metals on supports are preferably employed. All Pt(0) and Pt(II) compounds are preferred, and Pt-olefin complexes and Pt-vinylsiloxane complexes are preferred. Pt-Vinylsiloxane complexes, Pt-vinyldi- and tetrasiloxane complexes, which preferably have at least 2 or 4 olefinically unsaturated double bonds in the siloxane, are particularly preferred (see, for example, U.S. Pat. No. 3,715,334 incorporated herein by reference). The term siloxane includes in this connection polysiloxanes and/polyvinylsiloxanes.

It is additionally possible for component J) also to be a reactor product of reactive platinum compounds with the inhibitors H).

The amount of component J) in the formulation according to the present invention is preferably from 10 to 100 ppm, preferably 15 to 80 ppm and very particularly preferably 20 to 50 ppm, based on the total amount of components A) to I) and calculated on the basis of the metal of the platinum group in component J). The silicone-rubber formulations preferably comprise 20-100 ppm Pt, based on the amount of components A) to J), in the form of Pt salts, Pt complex compounds with nitrogen compounds, phosphorus compounds and/or alkene compounds or Pt metal on supports.

The active ingredient suspension K) can include on the one hand, preferably a polysiloxane of formula (I) indicated hereinbefore as a suspending agent. The definitions of the radicals therein are as follows

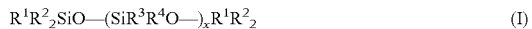

$R^1$ to $R^4$ are independently of one another particularly preferably each methyl and vinyl, where the polymer comprises from 0.0002 to 3% by weight of vinyl groups, and each molecule has at least two olefinically unsaturated multiple bonds.

x is particularly preferably varied so that the viscosity of the polymer extends from 0.1 to 1000 Pas at 25° C.

The suspension K) can comprise on the other hand, at least one antiseptic selected from the group of bispyridinium alkanes, of polymeric amidobiguanides, of quaternary ammonium compounds, in particular benzalkonium chloride, and chlorhexidine, taurolidine and triclosan preferably dispersed in an average particle size $d_{50}$ of from 0.5 to 15 μm, more preferably between 1 and 10 μm, and preferably having a particle size distribution from 0.1 to 30 μm, more preferably 0.5 to 20 μm.

Powdered antiseptics are usually supplied in micronized form. In order to incorporate them into the silicone rubbers, they are typically previously suspended in a suitable medium. Care must be taken in this connection that the medium is soluble in the silicone elastomer. Suitable for this purpose in one embodiment of the instant invention are, for example, commercially available silicone oils (R' and R" equal to alkyl), vinyl-terminated polydimethylsiloxanes (R' equal to vinyl; R' equal to methyl) or polyhydrosiloxanes (R' equal to H; R' equal to methyl), which generally have viscosities of from 100 to 1,000,000 mPas, preferably from 100 to 500,000 mPas at 25° C. The suitability is decided by whether the active ingredient/medium mixture can be sufficiently finely homogenized in a bead mill In one preferred embodiment, the suspending medium used is at least one vinyl group-terminated silicone polymer which is chemically incorporated into the silicone elastomer in a subsequent crosslinking reaction. It is thereby no longer possible for the suspending medium to be leached out into the surrounding body tissue or a body fluid where the silicone elastomer is used. For example, suitable vinyl group-terminated silicone polymers are available as polymer VS 200 (η(25° C.)=200 mPas; vinyl group content 0:25 mmol/g), polymer VS 1000 (η(25° C.)=1000 mPas; vinyl group content 0.11 mmol/g), or polymer VS 165 000 (η(25° C.)=165 000 mPas; vinyl group content 0.015 mmol/g), from Hanse-Chemie. Comparable products are available from other suppliers such as Dow Corning (Syl-Offe 7673: η(25° C.)=425 mPas) or Wacker Silicones (Dehesivee 920; η(25° C.)=500 mPas) or (Dehesivee 924; η (25° C.)=200 mPas).

"Expressly including each repeating unit" means that, in a deviation from the exact definition of the corresponding formula, that for example in the stated repeating units of the polymers employed according to the invention, of the formula (I), each individual $R^3$ or $R^4$ which occurs x times in one molecule can be selected in each case independently from the stated definitions and their preferred ranges, i.e. the radicals occurring in one molecule may be identical or different.

$C_1$-$C_{12}$-Alkyl for the purposes of the present invention are aliphatic hydrocarbon radicals having 1 to 12 carbon atoms, which may be straight-chain or branched. Examples which may be listed are methyl, ethyl, propyl, n-butyl, pentyl, hexyl, heptyl, nonyl, decyl, isopropyl, neopentyl, and 1,2,3-trimethylhexyl.

"$C_1$-$C_{12}$-Fluoroalkyl" means for the purposes of the present invention aliphatic hydrocarbon radicals having 1 to 12 carbon atoms, which may be straight-chain or branched and are substituted by at least one fluorine atom.

Examples which may be listed included perfluoroalkylethylene, 1,1,1-trifluoropropyl, 1,1,1-trifluorobutyl, and trifluoropropyl is preferred.

"Substituted phenyl" means for the purposes of the present invention phenyl radicals which are unsubstituted or mono- or polysubstituted by F, Cl, $CF_3$, $C_1$-$C_6$-alkyl, $C_1$-$C_6$-alkoxy, $C_3$-$C_7$-cycloalkyl, $C_2$-$C_6$-alkenyl or phenyl; phenyl is preferred.

Polymerization of a silicone-rubber formulations according to the present invention to give silicone rubber according to the invention can take place in principle at any temperature customary for this purpose. The polymerization preferably takes place at or in the neighbourhood of room temperature (20 to 25° C.).

It is known from the literature, e.g. the product brochure "Die platinkatalysierte Additionsvernetzung mit Elastosil R plus" from Wacker incorporated herein by reference, that inter alia amines impair the activity of the platinum catalyst in crosslinking.

However, it has surprisingly been found that the platinum catalyst retains its activity in the platinum-catalysed crosslinking of the silicone-rubber formulations according to the present invention despite the presence of amine groups. The mechanical properties found for silicone rubbers prepared from the silicone-rubber formulations according to the present invention were the same as for antiseptic-free comparison specimens. This finding allows such platinum catalysts to be used in the polymerization which is a substantial advantage over using peroxide catalysts.

To prepare the silicone rubbers according to the invention, it is possible in principle to use, apart from the silicone-rubber formulations which are described above and undergo platinum-catalysed crosslinking at room temperature, also heat-vulcanizable (HV) formulations which can be vulcanized at temperatures of about 200° C. with vulcanization catalysts on the basis such as benzoyl peroxide or di-p-chlorobenzoyl peroxide and require a thermal after treatment. Such silicone elastomers can be produced, for example, as described in U.S. Pat. Nos. 2,541,137 and/or 3,002,951, the contents of which are incorporated herein by reference in their entireties.

In addition, so-called single-component silicone-rubber formulations which are cured at room temperature on exposure to atmospheric humidity without further addition can also be used to prepare silicone rubbers according to the invention. These single-component formulations comprise mainly organopolysiloxanes having two terminal acyloxy, such as, for example, acetoxy, groups which hydrolyse on exposure to atmospheric humidity with formation of trifunctional siloxane units and act in the polymer as crosslinkers with formation of elastomers.

Silicone rubbers which undergo platinum-catalysed crosslinking at room temperature are preferred in the present invention. This is because using peroxide catalysts can cause the active ingredients employed to be chemically changed in the case of HV silicone-rubber systems at the required high vulcanization temperature and with use of peroxide catalysts. In addition, the catalyst residues which remain in the elastomer in the case of HV silicone-rubber systems might be responsible for toxic reactions in the body. Thus being able to use pt-based catalyst systems is highly advantageous and can be used without having to use peroxide based systems.

The acetic acid eliminated from usual moisture-curing silicone-rubber formulations as by product of the vulcanization at room temperature on exposure to atmospheric humidity may undergo unwanted side reactions with the active ingredient employed.

In a preferred embodiment, the present invention further relates to the silicone-rubber formulations described above wherein the polysiloxane A) is a polysiloxane of the formula (I)

(I)

in which the radicals $R^1$ and $R^2$ may in each case be identical or different, and are each $C_1$-$C_{12}$-alkyl, $C_1$-$C_{12}$-fluoroalkyl, and optionally substituted phenyl or naphthyl, $R^3$ and $R^4$ may in each case be identical or different, expressly including each repeating unit, and are each $C_1$-$C_{12}$-alkyl, $C_1$-$C_{12}$-fluoroalkyl and optionally substituted phenyl or naphthyl, $R^1$ and $R^3$ are additionally independently of one another $C_1$-$C_{12}$-alkenyl, in which case the polymer comprises from 0.0002 to 3% by weight of vinyl groups, and the molecule has at least two olefinically unsaturated multiple bonds, x is an integer from 2 to 15 000 and can vary so that the viscosity of the polymer extends from 0.1 to 1000 Pas at 25° C., a filler B) having a BET specific surface area of between 50 and 400 m²/g is used, the polyhydrosiloxane I) corresponds to the formula (II)

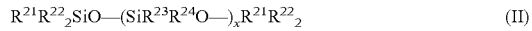
(II)

in which the substituents $R^{21}$ and $R^{22}$ may in each case be identical or different, and are each $C_1$-$C_{12}$-alkyl, $C_1$-$C_{12}$-fluoroalkyl, and optionally substituted phenyl or naphthyl, $R^{23}$ in each case expressly including each repeating unit independently of one another is hydrogen, $C_1$-$C_{12}$-alkyl, $C_1$-$C_{12}$-fluoroalkyl and optionally substituted phenyl or naphthyl, where $R^{23}$ is hydrogen in at least 4 of these silyldioxyl units so that a molecule has at least 4 crosslinking sites, $R^{24}$ in each case expressly including each repeating unit independently of one another is $C_1$-$C_{12}$-alkyl, $C_1$-$C_{12}$-fluoroalkyl and optionally substituted phenyl or naphthyl, x is an integer from 4 to 10 000 and is varied so that the viscosity of the polymer extends from 0.0005 to 0.1 Pas at 25° C., the catalyst from the platinum group J) is a catalyst which catalyses the hydrosilylation reaction and is selected from metals of the platinum group such as Pt, Rh, Ni, Ru, and compounds of metals of the platinum group, such as salts or complex compounds thereof, the suspending medium used for the suspension K) is at least one polysiloxane of the formula (I) according to A) in which the substituents R1 to R4 are each methyl and vinyl radicals, so that the polymer comprises from 0.0002 to 3% by weight of vinyl groups, and the molecule has at least two olefinically unsaturated multiple bonds, and x is varied so that the viscosity of the polymer extends from 0.1 to 1000 Pas at 25° C., and the suspension K) comprises at least one antiseptic selected from the group of bispyridinium alkanes, of polymeric amidobiguanides, of quaternary ammonium compounds, in particular benzalkonium chloride, and chlorhexidine, taurolidine and triclosan, which comprises in each case an average. particle size $d_{50}$ of from 0.5 to 15 µm, preferably between 1 and 10 µm, and a particle size distribution between 0.1 and 30 µm, preferably 0.5 to 20 µm.

Embodiments which are preferred, particularly preferred or very particularly preferred are those which make use of the parameters, compounds, definitions and explanations which are specified as preferred, particularly preferred or very particularly preferred.

However, the general definitions, parameters, compounds and explanations mentioned in the description, or definitions, parameters, compounds and explanations mentioned in preferred ranges, may also be combined with one another, that is to say between the respective ranges and preferred ranges, as desired.

Polymeric additives such as polyvinylpyrrolidone or polyethylene glycol can in principle be admixed if desired for any reason with the silicone rubbers up to a concentration for example of 5% by weight. In a preferred embodiment, such additives influencing the release to the surface are dispensed with.

The suspension K) can be produced by using conventional dissolvers which are employed as bead mill. Active ingredient, suspending medium and beads are put into the temperature-controlled vessel. In addition to the total volume, ⅓ glass beads can also be added. Instead of glass beads, it is also possible to use other grinding beads, e.g. made of zircon oxide.

The concentration of the active ingredient in the suspension K) can advantageously be from 10 to 40% by weight, preferably 15 to 35% by weight. The material for grinding can be heated to up to about 100° C. if desired in order to adjust the viscosity suitable for the grinding. However, the lowest possible temperature is generally always to be preferred in order to carry out the processing of the active ingredient under conditions which are as mild as possible.

The suspensions K) can be incorporated into the silicone-rubber matrix, for example, on a roll mixer. Their viscosity should preferably not be too low for this purpose because they flow away too easily. The risk associated with pastes which are too viscous is that they may be difficult to incorporate homogeneously into the silicone rubber.

The suspensions K) according to the invention therefore typically ought to have viscosities of from about 10,000 mPas to about 2,000,000 mPas at room temperature. Those preferably suitable for use for a process according to the invention advantageously have viscosities at 25° C. of from 20,000 to 1,000,000 mPas, particularly preferably from 50,000 to 500,000 mPas.

The active ingredients in the suspension K) according to the present invention usually have an average particle size $d_{50}$ of from 0.5 to 15 µm, preferably between 1 and 10 µm, and a particle size distribution between 0.1 to 30 µm, preferably 0.5 to 20 µm.

In addition, the suspensions K) produced in this viscosity range generally remain stable for several weeks and do not significantly sediment. It is possible in some cases to dispense with additional dispersion aids as desired.

In one embodiment components A)+F)+K) and I) are preferably present in the active ingredient-containing silicone-rubber mixtures according to the invention in a ratio of amounts such that the molar ratio of hydrogen directly linked to a silicon atom (SiH) in component I) to unsaturated radicals in components A), F) and K) is from 0.1 to 20, preferably from 0.8 to 10 and very particularly preferably from 1 to 5.

The suitable silicone-rubber formulation according to the instant invention preferably comprises components A) to K), with components B) to H) being optionally present. A silicone-rubber formulation according to the present invention preferably comprises component G) in addition to components A), I), J) and K).

In the rubber formulations according to the invention it is possible for ingredients A), polysiloxanes of the formula (I), and I), polyhydrosiloxanes of the formula (II), to be present completely or partly in component K), of the suspension, as suspending medium. Also included here according to the invention are formulations without separate further components A) and/or I).

The invention further relates to a process for producing the silicone-rubber formulations according to the invention, which is characterized in that initially components A) to J) are combined and mixed, and K) is then added and incorporated.

The suspension K) is added to the silicone-rubber compositions on a roll mixer, in a kneader or on an extruder. In a preferred embodiment, in the case of 2-component systems the two components are premixed and then the active ingredient suspension is added.

The silicone-rubber formulations according to the invention are preferably produced by adding the water repellents E) and F) which are optionally used, and optionally water, to component A), and incorporating component D) (filler) at temperatures of from 20 to 160° C. under a nitrogen atmosphere, and thus making the filler D) water-repellent by reaction with components E) and F). Subsequently, excess reaction products E) and F), and volatile reaction products therefrom (such as silanols, alcohols and water) are removed (preferably by heating at 150 to 170° C., where appropriate in vacuo). In the case of a two-component formulation, either component H) and I) or alternatively J) is metered into the resulting, preferably cooled mixture. If components C), D) and G) are required, they are metered after removal of the volatile components E) and F). In the case of the single-component formulation, H), I) and J) are metered in, the inhibitor H) being metered in first.

Conventional mixers are used, such as, for example, internal mixers, screw mixers, kneaders, preferably kneaders.

The crosslinkable silicone-rubber compositions according to the invention may moreover be 1-, 2- or else multicomponent systems. Multicomponent systems are for example those which comprise H), I) and J) separately.

The following examples serve to illustrate the invention without having a limiting effect.

EXAMPLES

Raw Materials:
Silicone Solid Rubbers for Urine Catheters
A 50:50 A/B 2K platinum-catalysed solid silicone-rubber system 3097/PA from Degania was used to produce the silicone Foley catheter shaft.

A component: vinyl group-terminated polydimethylsiloxane; comprises ingredients A), B) and J).

B component: polyhydrosiloxane; comprises ingredients B), G) and I).

The ratios of the amounts of ingredients A), B); G), I) and J) are adjusted in the A/B components so that the silicone elastomer has a shore A hardness of 65.

Silicone Solid Rubbers for Specimen Plates
A 1K platinum-catalysed addition-crosslinked solid silicone rubber Addisil 160 from GE Bayer Silicones was used for the laboratory test to produce specimen plates.

Suspending Medium
Polymer VS 1000: vinyl group-terminated polydimethylsiloxane from Hanse-Chemie; viscosity (at 25° C.)=1000 mPas; vinyl content: 0.11 mmol/g Active Ingredients
Octenidine dihydrochloride was purchased from PCAS, Turku, Finland, as a white powder with an average particle diameter of 15 µm in a purity of >98.5%.

Vantocil hydrochloride (PHMB) was purchased from Avecia as a pale yellow crystalline powder. It was ground before use, producing a colourless powder with an average particle size of 16 µm.

Examples 1-2

Production of the Active Ingredient Suspension in Polymer VS 1000:

A Dispermat F 105 dissolver from VMA Getzmann was used to produce the suspension. A plastic disc was used as grinding tool. The temperature of the temperature-controlled vessel was controlled using a thermostat from Julabo HC.

45 g of vinyl-terminated silicone polymer VS 1000, 15 g of active ingredient (see table) and 20 ml of zircon oxide beads with a diameter of about 2.8 mm are weighed into a 250 ml temperature-controlled vessel. The temperature of the vessel is controlled at 25° C. and the dissolver is introduced. The material to be ground is mixed at 8000/min for 20 minutes. The zircon oxide beads are then removed. A creamy white paste is obtained. The average particle diameter was determined. Results are shown below and at FIGS. 9 and 10.

| Active ingredient | Concentration | Average particle size $d_{50}$ |
|---|---|---|
| Example 1 octenidine dihydrochloride | 25% by weight | 1.7 µm |
| Example 2 PHMB | 25% by weight | 9.2 µm |

Example 3

The thermal stability of the octenidine dihydrochloride suspension from Example 1 was determined by thermogravimetric analysis (TGA). Results are show at FIG. 11.

The suspension is thermally stable up to at least 200° C., so that the crosslinking reaction to be carried out at 170° C. after mixing into the silicone rubber can take place without problems of stability of the active ingredient or of the suspending medium.

Examples 4-7

The solid silicone rubber Addisil 160 was put onto a roll mixer from Vogt (2 rolls; roll diameter 80 mm, roll width 280 mm; operating width 200 mm) with cooling at room temperature. The front rotating roll was operated at 16.5 min$^{-1}$, and the rear roll at 20 min$^{-1}$. The active ingredients were subsequently mixed in by adding the amounts, indicated in the table, of the active ingredient suspension from Example 1 or 2 into the roll gap, and continuing the mixing until the suspension was homogeneously incorporated. The active ingredient-containing silicone rubber was then removed as sheet about 2 mm thick from the roll.

|  | Silicone rubber Addisil 160 in g | Octenidine dihydrochloride suspension based on Polymer VS 1000 Amount of suspension | Active ingredient concentration |
|---|---|---|---|
| Example 4 | 96 | 4 g suspension from Example 1 | 1% by weight |
| Example 5 | 92 | 8 g suspension from Example 1 | 2% by weight |

|  | Silicone rubber Addisil 160 in g | PHMB suspension based on Polymer VS 1000 Amount of suspension | Active ingredient concentration |
|---|---|---|---|
| Example 6 | 96 | 4 g suspension from Example 2 | 1% by weight |
| Example 7 | 92 | 8 g suspension from Example 2 | 2% by weight |

The respective boards were then heated at 170° C. for 2 hours for curing (crosslinking).

Example 8

Active Ingredient Distribution

Figure 1:
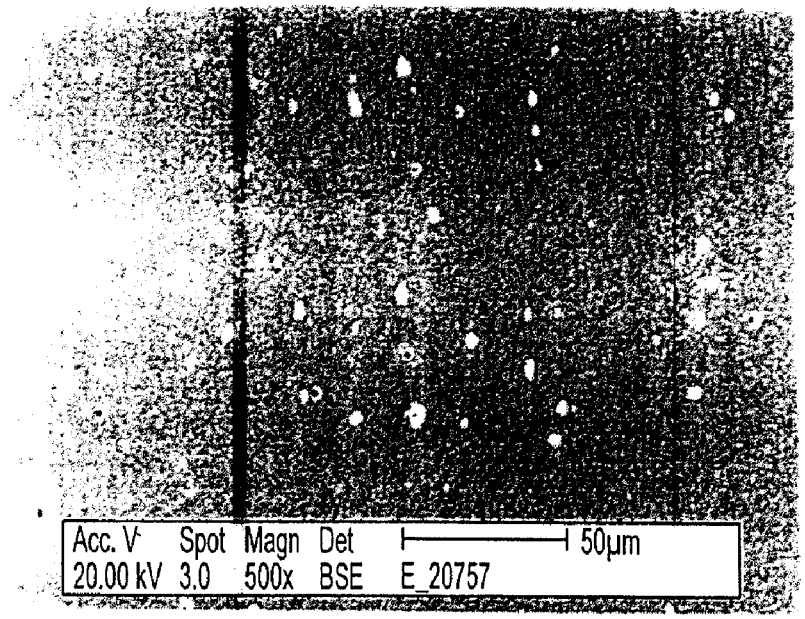
FIGS. 1 and 2 are SEM micrographs of silicone elastomers according to the present invention.
Figure 2:
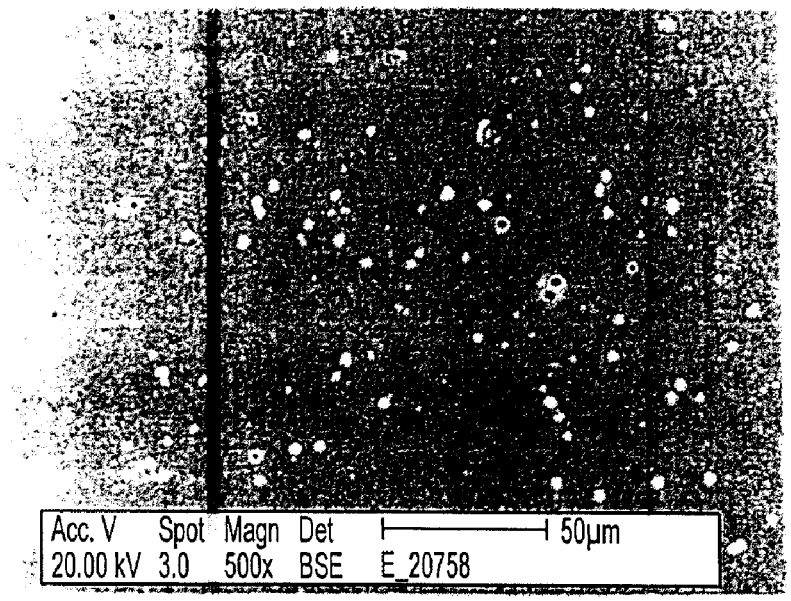

It is possible by scanning electron micrographs coupled to EDX to visualize specifically, by chlorine detection, only the active ingredient particles in the silicone elastomer matrix. FIGS. 1 and 2 show scanning electron micrographs of the silicone elastomer specimen plates from Example 6 (1% by weight PHMB) and Example 7 (2% by weight PHMB) (PHMB active ingredient particles appear pale). The films show that the active ingredient is distributed homogeneously and as very fine particles about 1 to 5 µm in size in the silicone elastomer matrix.

Example 9

Continuity of the Surface Protection of the PHMB-Containing Silicone Elastomer Plates The elution tests were carried out with the active ingredient-containing silicone elastomer boards from Examples 6 and 7, which were cut into pieces 1 cm$^2$ in size. The samples each weighed about 2.1 g and had a surface area of about 22 or 25 cm$^2$. 16 ml of demineralized water were used as elution medium. The elution medium was replaced by new water in each case after 1 h, 4 h, 8 h, 24 h, 48 h, 120 h and 360 hours (15 days), and the active ingredient content in the solutions was determined.

| Hours | Specimen from Example 6 [µg/g*cm$^2$] | Specimen from Example 7 [µg/g*cm$^2$] |
|---|---|---|
| 1.00 | 0.810 | 2.19 |
| 4.00 | 0.980 | 2.36 |
| 8.00 | 1.150 | 2.53 |
| 24.00 | 1.320 | 2.70 |
| 48.00 | 1.490 | 2.87 |
| 120.00 | 1.660 | 3.20 |
| 360.00 | 1.830 | 3.43 |

During the investigation there is diffusion of the active ingredient to the surface of the sample body, thus ensuring continuous protection of the surface against colonization by bacteria and yeasts.

Example 10

Continuity of the Surface Protection of the Octenidine Dihydrochloride-Containing Silicone Elastomer Plates The elution tests were carried out with the boards from Examples 4 and 5 which were cut into pieces 1 cm$^2$ in size. The samples each weighed about 2.0 g and had a surface area of about 35 cm$^2$. 16 ml of demineralized water were used as elution medium. The elution medium was replaced in each case by new water after 1 h, 4 h, 8 h, 24 h, 48 h, 120 h and 360 hours (15 days), and the active ingredient content in the solutions was determined.

| Hours | Specimen from Example 4 [µg/g*cm$^2$] | Specimen from Example 5 [µg/g*cm$^2$] |
|---|---|---|
| 1.00 | 1.72 | 0.01 |
| 4.00 | 2.33 | 0.02 |
| 8.00 | 2.61 | 0.03 |
| 24.00 | 3.59 | 0.04 |
| 48.00 | 4.04 | 0.05 |
| 120.00 | 4.05 | 0.06 |
| 360.00 | 4.27 | 0.07 |

During the investigation there is diffusion of the active ingredient to the surface of the sample body, thus ensuring continuous protection of the surface against colonization by bacteria and yeasts.

The samples release small amounts of active ingredient over 15 days, the amount being far away from a pharmacologically effective dose.

Example 11

Microbiological Assessment of the Samples from Examples 4 to 5

Test plates with a diameter of about 5 mm were cut out of the active ingredient-containing silicone elastomer boards of Examples 4 and 5 and sterilized by gamma radiation. The sterile test plates were used to carry out the following microbiological tests.

1. Method

The antibacterial effect was investigated with the aid of the agar diffusion test.

1.1. Test Plates 18 ml of NCCLS-compliant Mueller-Hinton agar (Merck KGaA Darmstadt/Lot ZC217935 430) were poured into 9 cm-diameter Petri dishes.

1.2. Bacterial Suspension

A suspension with a McFarland density of 0.5 in 0.85% NaCl solution was prepared from an overnight culture of the test strain on Columbia blood agar. A "colony pool" of 3 to 4 colonies dabbed with an inoculating loop was used for the suspension.

1.3. Test Mixture

A sterile cotton swab is dipped in the suspension. The excess liquid is squeezed out on the edge of the glass. The swab is used to inoculate the Mueller-Hinton agar plate uniformly in three directions at an angle of 60° in each case. The material samples are then placed on the test plate. The test plates were incubated at 37° C. for 24 hours. The antibacterial effect of the samples was assessed on the basis of zones of inhibition.

2.2. Test Strains

The test strains selected were representatively Gram-negative rods, an MRSA (*Staphylococcus aureus* MRSA 1150-93) and a *Candida* species (*Candida albicans* ATCC 14053).

3. Results

A zone of inhibition was detectable with the samples of Examples 4 and 5. The active ingredient in the silicone material thus prevents bacterial growth.

The effect on the yeast-like fungus *Candida albicans* is particularly noteworthy.

Figure 3:
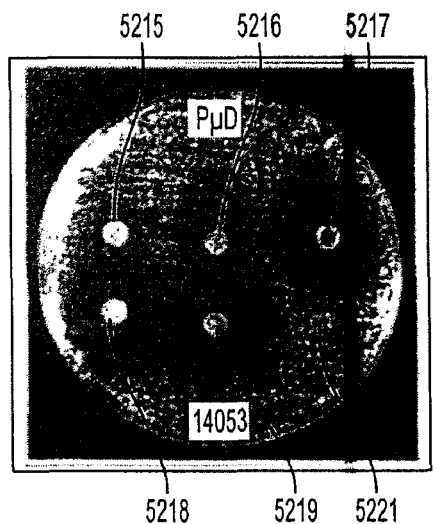
FIGS. 3-8 are depictions showing zones of inhibitor showing the antibacterials effect of the present invention.
Figure 4:
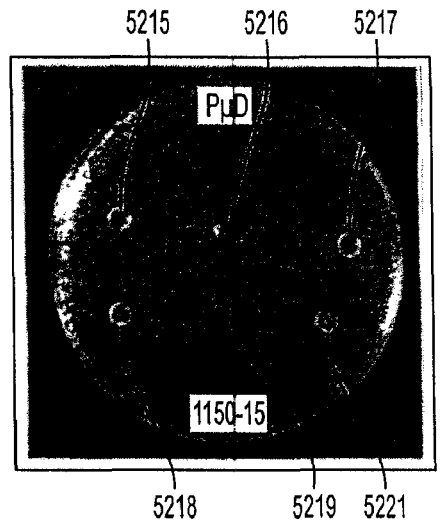

FIGS. 3 and 4 document the result of the tests. In these, FIG. 3 shows the zones of inhibition for *Candida albicans* ATCC 14053 with the samples from Example 4 (5217) and 5 (5219), and FIG. 4 shows the zones of inhibition for *Staphylococcus aureus* MRSA 1150-93 with the samples from Example 4 (5217) and 5 (5219).

Example 12

Microbiological Assessment of the Samples from Examples 6 to 7

Test plates with a diameter of about 5 mm were cut out of the active ingredient-containing silicone elastomer boards of Examples 6 and 7 and sterilized by gamma radiation. The sterile test plates were used to carry out the following microbiological tests.

1. Method

The antibacterial effect was investigated with the aid of the agar diffusion test.

1.1. Test Plates 18 nil of NCCLS-compliant Mueller-Hinton agar (Merck KGaA Darmstadt/Lot ZC217935 430) were poured into 9 cm-diameter Petri dishes.

1.2. Bacterial Suspension

A suspension with a McFarland density of 0.5 in 0.85% NaCl solution was prepared from an overnight culture of the test strain on Columbia blood agar. A "colony pool" of 3 to 4 colonies dabbed with an inoculating loop was used for the suspension.

1.3. Test Mixture

A sterile cotton swab is dipped in the suspension. The excess liquid is squeezed out on the edge of the glass. The swab is used to inoculate the Mueller-Hinton agar plate uniformly in three directions at an angle of 60° in each case. The material samples are then placed on the test plate. The test plates were incubated at 37° C. for 24 hours. The antibacterial effect of the samples was assessed on the basis of zones of inhibition.

2.2. Test Strains

The test strains selected were representatively ATCC strains of three Gram-negative rods, a *Staphylococcus aureus*, an MRSA strain and a *Candida* species.

3. Results

| gram – rods | 35218 | *Eschericia coli* ATCC 35218 |
|---|---|---|
| | 35659 | *Proteus mirabilis* ATCC 35659 |
| | 27853 | *Pseudomonas aeruginosa* ATCC 27853 |
| Gram + cocci | 29213 | *Staphylococcus aureus* ATCC 29213 |
| | 0134 - 93 | *Staphylococcus aureus* MRSA 0134 - 93 |
| yeast-like fungus | 14053 | *Candida albicans* ATCC 14053 |

Figure 5:
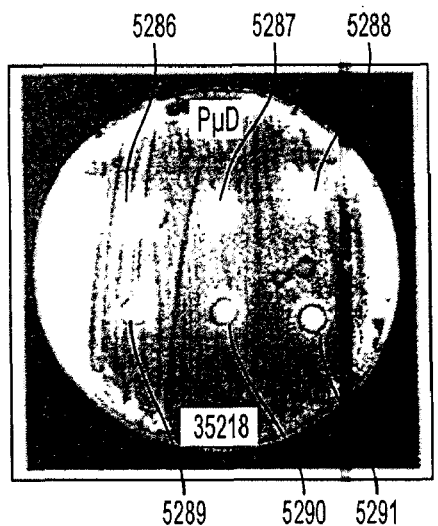
Figure 6:
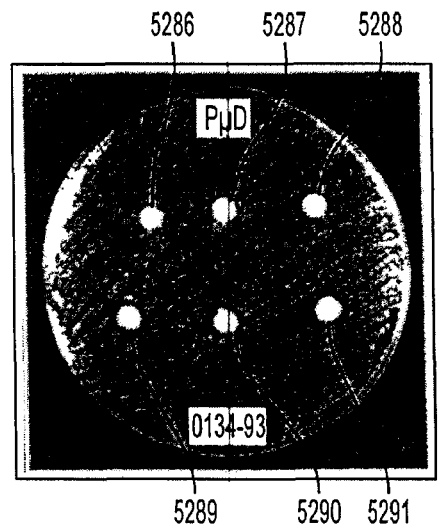
Figure 7:
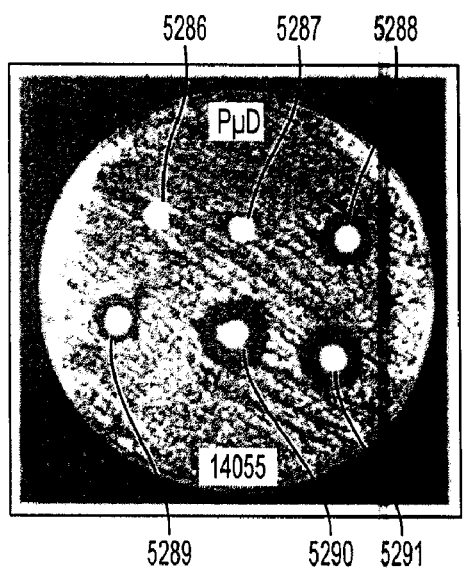
Figure 8:
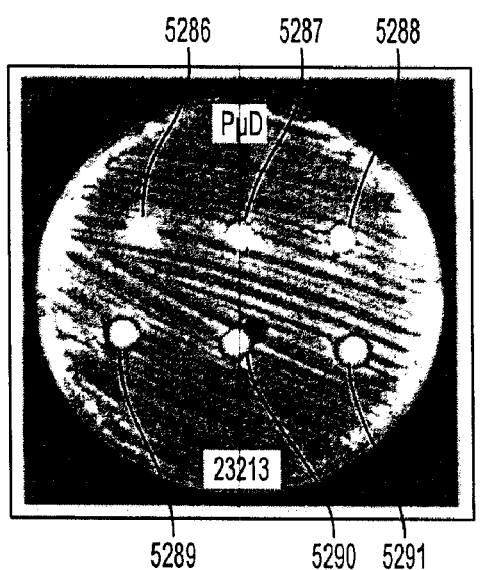

The antibacterial effect of the samples was detectable by means of the zones of inhibition. FIGS. 5 to 8 document the results. FIG. 5 shows the zones of inhibition for *Escherichia coli* ATCC 35218 with the samples from Example 6 (5289) and 7 (5291). FIG. 6 shows the zones of inhibition for *Staphylococcus aureus* MRSA 0134-93 with the samples from Example 6 (5289) and 7 (5291). FIG. 7 shows the zones of inhibition for *Candida albicans* ATCC 14053 with the samples from Example 6 (5289) and 7 (5291). FIG. 8 shows the zones of inhibition for *Staphylococcus aureus* ATCC 29213 with the samples from Example 6 (5289) and 7 (5291).

Example 13

The active ingredient suspension from Example 1 was mixed into the A/B 2 K platinum-catalysed addition-crosslinking silicone-rubber system supplied by Degania on a calender kneader, and the octenidine dihydrochloride-containing silicone rubber was then further processed to Foley catheter shafts with 1% by weight octenidine dihydrochloride.

Example 14

Continuity of the surface protection of the octenidine dihydrochloride—containing silicone elastomer Foley catheter shafts.

The elution tests were carried out with the shafts from Example 13, which were cut into pieces 2 cm long. The samples each weighed about 2.0 g and had a surface area of about 33 cm$^2$.

16 ml of simulated urine of the following composition was used as elution medium

| Urea | 1.94% |
|---|---|
| NaCl | 0.84% |
| MgSO$_4$, heptahydrate | 0.11% |
| CaCl$_2$ | 0.06% |

The elution medium was replaced in each case after 1 h, 4 h, 8 h, 24 h, 48 h, 120 h and 360 hours (15 days), and the active ingredient content in the solutions was determined.

| | Foley catheter shaft from Example 13 |
|---|---|
| Lot | 5050419 |
| Octenidine 2 × HCl conc. | 1% |
| Weight: | 1.93 g |
| Surface | 33.35 cm$^2$ |
| 1 h | 0.44 mg/l |
| 4 h | 0.540 mg/l |

-continued

| | Foley catheter shaft from Example 13 |
|---|---|
| 8 h | 0.710 mg/l |
| 24 h | 1.150 mg/l |
| 48 h | 1.460 mg/l |
| 120 h | 1.610 mg/l |
| 360 h | 2.050 mg/l |

Diffusion of the active ingredient to the surface of the sample body takes place during the investigation and thus ensures continuous protection of the surface colonization with bacteria and yeasts.

The samples release small amounts of active ingredient over 15 days, the amount being far away from a pharmacologically effective dose.

Example 15

Biocompatibility Tests as Specified in DIN ISO 10993-5 (1999), EN 30993-5 (1994)

The catheter shafts from Example 13 were for this purpose extracted non-sterile at 37° C. and 5% $pCO_2$ in extraction medium (DMEM including antibiotics without FCS) for 24 h. The surface-volume ratio was 1 $cm^2$/ml of extraction medium. After completion of the extraction, the extraction medium was sterilized by filtration and supplemented with sterile FCS (final concentration: 10% FCS in the extraction medium). The FCS-supplemented extraction medium was put sterile on precultured L 929 mouse fibroblast cells and incubated at 37° C., 5% $pCO_2$ for 48 h. The extract was subjected to quadruplicate parallel testing.

Triton X 100 was added to the L929 cells used as toxic positive control (final concentration 1%). Cell culture medium served as non-toxic negative control.

After the 48-hour incubation, the release of lactate dehydrogenase (LDH) in the cell culture supernatant was measured by a photometric method. The cells were then subjected to alkaline lysis and the protein content was measured by the Bradford method.

The cells were fixed and stained with methylene blue to determine the cell count. After acidic extraction of the methylene blue, the dye content was ascertained by photometry and the extinction was compared with a standard curve in order to determine the cell count on the basis of the dye concentration. Results are shown at FIG. 12.

The value of the positive control was 0.5% of the negative control value and is thus in the valid range below 35% relative to the culture medium control.

Values of cell counts for extracts which were more than 19% below the value of the cell count for the negative control are regarded as cytotoxic. This is not the case in the present extract of the sample from Example 13. The material extract shows no cytotoxic reaction. Results are shown at FIG. 13.

The value of the positive control is 6.8% of the negative control value and is thus in the valid range below 35% relative to the culture medium control.

Protein levels in extracts which are more than 19% less than the level of the protein content in the negative control are regarded as cytotoxic. This is not the case in the present extract of the sample from Example 13. The material extract shows no cytotoxic reaction. Results are shown at FIG. 14.

In contrast to Triton X 100 in the cell culture medium, the specific LDH activity is increased more than 31-fold compared with the negative control (medium).

The sample from Example 13 has no cytotoxic effect.

Additional advantages, features and modifications will readily occur to those skilled in the art. Therefore, the invention in its broader aspects is not limited to the specific details, and representative devices, shown and described herein. Accordingly, various modifications may be made without department from the spirit or scope of the general inventive concept as defined by the appended claims and their equivalents.

All documents referred to herein are specifically incorporated herein by reference in their entireties.

The use of singular article terms including "an", "a" and "the" can connote the singular or plural of the object that follows.

The invention claimed is:

1. A silicone elastomer comprising at least one silicone elastomer and an antiseptic suspension,
   wherein said antiseptic suspension is incorporated into the at least one silicone elastomer so as to distribute the at least one antiseptic homogeneously therein, the antiseptic suspension consisting of:
   a suspending medium,
   at least one antiseptic, and
   optionally a non-functional polysiloxane,
   wherein:
   a. said suspending medium consists of at least one polysiloxane that is chemically incorporated into the at least one silicone elastomer in a crosslinking reaction, the at least one polysiloxane being selected from the group consisting of:
   (i) a polysiloxane according to formula (I):

   $$R^1R^2_2SiO\text{—}(SiR^3R^4O\text{—})_xR^1R^2_2 \qquad (I),$$

wherein:
   $R^1$ is selected from the group consisting of: $C_1$-$C_{12}$-alkyl, $C_1$-$C_{12}$-alkenyl, $C_1$-$C_{12}$-fluoroalkyl, optionally substituted phenyl, and optionally substituted naphthyl;
   $R^2$ is selected from the group consisting of: $C_1$-$C_{12}$-alkyl, $C_1$-$C_{12}$-fluoroalkyl, optionally substituted phenyl, and optionally substituted naphthyl;
   wherein $R^1$ and $R^2$ may in each case be identical or different;
   $R^3$ is selected from the group consisting of: $C_1$-$C_{12}$-alkyl; $C_1$-$C_{12}$-alkenyl; $C_1$-$C_{12}$-fluoroalkyl; optionally substituted phenyl; optionally substituted naphthyl; and —$OSiR^2R^3R'$, in which R' symbolizes the continuation of the siloxane chain of formula (I) in the branching so that the polysiloxane may have branching units of the formula $SiO_{4/2}$ and $R^3SiO_{3/2}$;
   $R^4$ is selected from the group consisting of: $C_1$-$C_{12}$-alkyl, $C_1$-$C_{12}$-fluoroalkyl, optionally substituted phenyl, and optionally substituted naphthyl; and —$OSiR^2R^3R'$, in which R' symbolizes the continuation of the siloxane chain of formula (I) in the branching so that the polysiloxane may have branching units of the formula $SiO_{4/2}$ and $R^3SiO_{3/2}$;
   wherein $R^3$ and $R^4$ may in each case be identical or different, expressly including each repeating unit;
   x is an integer from 2 to 15,000 and is varied so that the polysiloxane has a viscosity at 25° C. from 0.1 to 1000 Pas at 25° C.;
   with the proviso that, if $R^1$ or $R^3$ is $C_1$-$C_{12}$-alkenyl, then the polysiloxane of formula I shall comprise from 0.0002 to 3% by weight of vinyl groups and at least two double bonds;

and (ii) a polyhydrosiloxane of the formula (II)

$$R^{21}R^{22}{}_2SiO\text{---}(SiR^{23}R^{24}O\text{---})_xR^{21}R^{22}{}_2 \quad (II),$$

wherein:
- $R^{21}$ and $R^{22}$ are selected from the group consisting of $C_1\text{-}C_{12}$-alkyl, wherein $R^{21}$ and $R^{22}$ may in each case be identical or different, and;
- $R^{23}$ in each case expressly including each repeating unit independently of one another is selected from the group consisting of: hydrogen; $C_1\text{-}C_{12}$-alkyl; $C_1\text{-}C_{12}$-fluoroalkyl; optionally substituted phenyl; optionally substituted naphthyl; and —OSiR$^{23}$R$^{24}$R″ in which R″ symbolizes the continuation of the siloxane chain such that the polyhydrosiloxane has branching units of the formula $SiO_{4/2}$ and $R^{23}SiO_{3/2}$, wherein $R^{23}$ in at least 4 of these silyldioxy units is hydrogen so that a molecule has at least 4 crosslinking sites,
- $R^{24}$ in each case expressly including each repeating unit independently of one another is selected from the group consisting of $C_1\text{-}C_{12}$-alkyl; $C_1\text{-}C_{12}$-fluoroalkyl; optionally substituted phenyl; optionally substituted naphthyl; and —OSiR$^{23}$R$^{24}$R′″ in which R′″ the continuation of the siloxane chain of formula (II) in the branching so that the polymer molecule has branching units of the formula $SiO_{4/2}$ and $R^{23}SiO_{3/2}$,
- Y is an integer from 4 to 10,000 and is varied so that the polyhydrosiloxane has a viscosity at 25° C. from 0.0005 to 0.1 Pas;

and, b. said at least one antiseptic is selected from the group consisting of bispyridinium alkanes, polymeric amidobiguanides, and quaternary ammonium compounds in an average particle size $d_{50}$ of from 0.5 to 15 μm and a particle size distribution from 0.1-30 μm.

2. A method for producing a medical article comprising obtaining a silicone elastomer of claim 1 and using said elastomer to produce said article.

3. A catheter comprising a silicone elastomer according to claim 1.

4. A medical device comprising a silicone elastomer of claim 1.

5. A silicone elastomer of claim 1 wherein said antiseptic is selected from the group consisting of benzalkonium chloride, chlorhexidine, taurolidine and triclosan.

6. The silicone elastomer of claim 1, wherein the suspending medium comprises at least one vinyl-terminated silicone polymer.

7. The silicone elastomer of claim 1, wherein the silicon elastomer inhibits surface colonization by microorganisms for 15 days.

8. A silicone-rubber formulation comprising
A) at least one polysiloxane of formula (I)

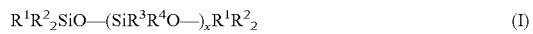

$$R^1R^2{}_2SiO\text{---}(SiR^3R^4O\text{---})_xR^1R^2{}_2 \quad (I)$$

wherein
- $R^1$ is selected from the group consisting of $C_1\text{-}C_{12}$-alkyl, $C_1\text{-}C_{12}$-alkenyl, $C_1\text{-}C_{12}$-fluoroalkyl, and optionally substituted phenyl or naphthyl, which may in each case be identical or different,
- $R^2$ is selected from the group consisting of $C_1\text{-}C_{12}$-alkyl, $C_1\text{-}C_{12}$-fluoroalkyl, and optionally substituted phenyl or naphthyl, which may in each case be identical or different,
- $R^3$ is selected from the group consisting of $C_1\text{-}C_{12}$-alkyl, $C_1\text{-}C_{12}$-alkenyl, $C_1\text{-}C_{12}$-fluoroalkyl and optionally substituted phenyl or naphthyl, and additionally —OSiR$^2$R$^3$R, in which R symbolizes the continuation of the siloxane chain in analogy to formula (I) in the branching so that the polysiloxane may have branching units of the formula $SiO_{4/2}$ and $R^3SiO_{3/2}$, which may in each case be identical or different, expressly including each repeating unit,
- $R^4$ is selected from the group consisting of $C_1\text{-}C_{12}$-alkyl, $C_1\text{-}C_{12}$-fluoroalkyl and optionally substituted phenyl or naphthyl, and additionally —OSiR$^2$R$^3$R, in which R symbolizes the continuation of the siloxane chain in analogy to formula (I) in the branching so that the polysiloxane may have branching units of the formula $SiO_{4/2}$ and $R^3SiO_{3/2}$, which may in each case be identical or different, expressly including each repeating unit,
- with the proviso that, if $R^1$ or $R^3$ is in any case $C_1\text{-}C_{12}$-alkenyl, then the polymer comprises from 0.0002 to 3% by weight of vinyl groups, and the polysiloxane has at least two olefinically unsaturated multiple bonds,
- x is an integer from 2 to 15 000 and can vary such that the viscosity of the polysiloxane extends from 0.1 to 1000 Pas at 25° C., I) at least one polyhydrosiloxane of formula (II)

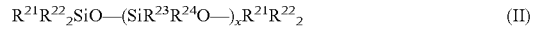

$$R^{21}R^{22}{}_2SiO\text{---}(SiR^{23}R^{24}O\text{---})_xR^{21}R^{22}{}_2 \quad (II)$$

wherein
- $R^{21}$ and $R^{22}$ may in each case be identical or different, and are each $C_1\text{-}C_{12}$-alkyl, $C_1\text{-}C_{12}$-fluoroalkyl, and optionally substituted phenyl or naphthyl,
- $R^{23}$ in each case expressly including each repeating unit independently of one another is hydrogen, $C_1\text{-}C_{12}$-alkyl, $C_1\text{-}C_{12}$-fluoroalkyl and optionally substituted phenyl or naphthyl, additionally —OSiR$^{23}$R$^{24}$R in which R symbolizes the continuation of the siloxane chain in analogy to formula (II) in the branching so that the polyhydrosiloxane may have branching units of the formula $SiO_{4/2}$ and $R^{23}SiO_{3/2}$, where $R^{23}$ in at least 4 of these silyldioxyl units is hydrogen to provide at least 4 crosslinking sites,
- in each case expressly including each repeating unit independently of one another is $C_1\text{-}C_{12}$-alkyl, $C_1\text{-}C_{12}$-fluoroalkyl and optionally substituted phenyl or naphthyl, additionally —OSiR$^{23}$R$^{24}$R in which R symbolizes the continuation of the siloxane chain in analogy to formula (II) in the branching so that the polyhydrosiloxane may have branching units of the formula $SiO_{4/2}$ and $R^{23}SiO_{3/2}$,
- x is an integer from 4 to 10 000 and is varied so that the viscosity of the polymer extends from 0.0005 to 0.1 Pas at 25° C., J) at least one catalyst comprising an element of the platinum group, said catalyst having a maximum of 3 parts by weight of metal compounds, salts, and complex compounds of Fe, Al, Zn, Ti, Zr, Ce or other lanthanoids based on 100 parts by weight of component A), K) at least one antiseptic suspension consisting of:
a suspending medium,
at least one antiseptic, and
optionally a non-functional polysiloxane,
wherein:
a. said suspending medium consists of at least one polysiloxane selected from the group consisting of the polysiloxane according to formula (I) and the polyhydrosiloxane of the formula (II), wherein the suspending medium is chemically incorporated into said A) in a crosslinking reaction; and b. said at least one antiseptic is selected from the group consisting of bispyridinium alkanes, polymeric amidobiguanides, and quaternary ammonium compounds in an average particle size $d_{50}$ of from 0.5 to 15 µm and a particle size distribution from 0.1-30 µm.

9. A silicone-rubber formulation according to claim 8, wherein the polysiloxane A) is a polysiloxane of formula (I)

wherein
$R^1$ is selected from the group consisting of $C_1$-$C_{12}$-alkyl, $C_1$-$C_{12}$-alkenyl, $C_1$-$C_{12}$-fluoroalkyl, and optionally substituted phenyl or naphthyl, which may in each case be identical or different,
$R^3$ is selected from the group consisting of $C_1$-$C_{12}$-alkyl, $C_1$-$C_{12}$-alkenyl, $C_1$-$C_{12}$-fluoroalkyl and optionally substituted phenyl or naphthyl, which may in each case be identical or different, expressly including each repeating unit,
$R^4$ is selected from the group consisting of $C_1$-$C_{12}$-alkyl, $C_1$-$C_{12}$-fluoroalkyl and optionally substituted phenyl or naphthyl, which may in each case be identical or different, expressly including each repeating unit,
with the proviso that, if $R^1$ or $R^3$ is in any case $C_1$-$C_{12}$-alkenyl, then the polysiloxane comprises from 0.0002 to 3% by weight of vinyl groups, and has at least two olefinically unsaturated multiple bonds,
x is an integer from 2 to 15,000 and can vary such that the viscosity of the polysiloxane extends from 0.1 to 1000 Pas at 25° C.,
a filler having a BET specific surface area of from 50 to 400 m²/g is used,
the polyhydrosiloxane I) corresponds to formula (II)

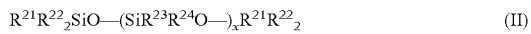

wherein
$R^{21}$ and $R^{22}$ may in each case be identical or different, and are each $C_1$-$C_{12}$-alkyl, $C_1$-$C_{12}$-fluoroalkyl, and optionally substituted phenyl or naphthyl,
$R^{23}$ in each case expressly including each repeating unit independently of one another is hydrogen, $C_1$-$C_{12}$-alkyl, $C_1$-$C_{12}$-fluoroalkyl and optionally substituted phenyl or naphthyl, where $R^{23}$ is hydrogen in at least 4 of these silyldioxyl units so that said polyhydrosiloxane has at least 4 crosslinking sites,
$R^{24}$ in each case expressly including each repeating unit independently of one another is $C_1$-$C_{12}$-alkyl, $C_1$-$C_{12}$-fluoroalkyl and optionally substituted phenyl or naphthyl,
x is an integer from 4 to 10,000 and is varied so that the viscosity of the polyhydrosiloxane extends from 0.0005 to 0.1 Pas at 25° C.,
the catalyst from the platinum group J) is a catalyst which catalysts a hydrosilylation reaction and is selected from the range consisting of metals of the platinum group such and compounds of metals of the platinum group, including salts and/or complex compound metals,
the suspending medium used for the suspension K) is at least one polysiloxane of formula (I) according to A) wherein the substituents $R^1$ to $R^4$ are each methyl and vinyl radicals, so that the polysiloxane comprises from 0.0002 to 3% by weight of vinyl groups, and polysiloxane has at least two olefinically unsaturated multiple bonds, and x is varied so that the viscosity of the polysiloxane extends from 0.1 to 1000 Pas at 25° C., and the antiseptic suspension K) comprises at least one antiseptic selected from the group consisting of chlorhexidine, octenidine, PHMB, quats, taurolidine and triclosan.

10. A process for preparing a silicone elastomer comprising providing a silicone-rubber formulation according to claim 8 and polymerizing said silicone-rubber formulation to produce said elastomer.

11. A process for preparing a silicone elastomer comprising providing a silicone rubber formulation according to claim 9 polymerizing said silicone rubber formulation to produce said elastomer.

12. A silicone rubber formulation of claim 8, wherein the molar ratio of hydrogen directly linked to a silicone atom in component I to unsaturated radicals in components A and K is from 01 to 20.

13. A method for rendering a polysiloxane elastomer resistant to colonization by microorganisms comprising
generating an antiseptic suspension, the antiseptic suspension consisting of:
a suspending medium,
at least one antiseptic, and
optionally a non-functional polysiloxane,
wherein:
a. said suspending medium consists of at least one polysiloxane selected from the group consisting of:
(i) a polysiloxane according to formula (I):

wherein:
$R^1$ is selected from the group consisting of: $C_1$-$C_{12}$-alkyl, $C_1$-$C_{12}$-alkenyl, $C_1$-$C_{12}$-fluoroalkyl, optionally substituted phenyl, and optionally substituted naphthyl;
$R^2$ is selected from the group consisting of: $C_1$-$C_{12}$-alkyl, $C_1$-$C_{12}$-fluoroalkyl, optionally substituted phenyl, and optionally substituted naphthyl;
wherein $R^1$ and $R^2$ may in each case be identical or different;
$R^3$ is selected from the group consisting of: $C_1$-$C_{12}$-alkyl; $C_1$-$C_{12}$-alkenyl; $C_1$-$C_{12}$-fluoroalkyl; optionally substituted phenyl; optionally substituted naphthyl; and —OSiR²R³R', in which R' symbolizes the continuation of the siloxane chain of formula (I) in the branching so that the polysiloxane may have branching units of the formula $SiO_{4/2}$ and $R^3SiO_{3/2}$;
$R^4$ is selected from the group consisting of: $C_1$-$C_{12}$-alkyl, $C_1$-$C_{12}$-fluoroalkyl, optionally substituted phenyl, and optionally substituted naphthyl; and —OSiR²R³R', in which R' symbolizes the continuation of the siloxane chain of formula (I) in the branching so that the polysiloxane may have branching units of the formula $SiO_{4/2}$ and $R^3SiO_{3/2}$;
wherein $R^3$ and $R^4$ may in each case be identical or different, expressly including each repeating unit;
x is an integer from 2 to 15,000 and is varied so that the polysiloxane has a viscosity at 25° C. from 0.1 to 1000 Pas at 25° C.;
with the proviso that, if $R^1$ or $R^3$ is $C_1$-$C_{12}$-alkenyl, then the polysiloxane of formula I shall comprise from 0.0002 to 3% by weight of vinyl groups and at least two double bonds;

and (ii) a polyhydrosiloxane of the formula (II)

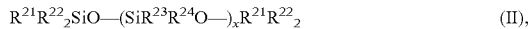
(II), wherein:

$R^{21}$ and $R^{22}$ are selected from the group consisting of $C_1$-$C_{12}$-alkyl, wherein $R^{21}$ and $R^{22}$ may in each case be identical or different, and;

$R^{23}$ in each case expressly including each repeating unit independently of one another is selected from the group consisting of: hydrogen; $C_1$-$C_{12}$-alkyl; $C_1$-$C_{12}$-fluoroalkyl; optionally substituted phenyl; optionally substituted naphthyl; and —OSiR$^{23}$R$^{24}$R" in which R" symbolizes the continuation of the siloxane chain such that the polyhydrosiloxane has branching units of the formula $SiO_{4/2}$ and $R^{23}SiO_{3/2}$, wherein $R^{23}$ in at least 4 of these silyldioxy units is hydrogen so that a molecule has at least 4 crosslinking sites, $R^{24}$ in each case expressly including each repeating unit independently of one another is selected from the group consisting of $C_1$-$C_{12}$-alkyl; $C_1$-$C_{12}$-fluoroalkyl; optionally substituted phenyl; optionally substituted naphthyl; and —OSiR$^{23}$R$^{24}$R''' in which R''' the continuation of the siloxane chain of formula (II) in the branching so that the polymer molecule has branching units of the formula $SiO_{4/2}$ and $R^{23}SiO_{3/2}$, Y is an integer from 4 to 10,000 and is varied so that the polyhydrosiloxane has a viscosity at 25° C. from 0.0005 to 0.1 Pas;

and, b. said at least one antiseptic is selected from the group consisting of bispyridinium alkanes, polymeric amidobiguanides, and quaternary ammonium compounds in an average particle size $d_{50}$ of from 0.5 to 15 μm and a particle size distribution from 0.1-30 μm; and chemically incorporating said antiseptic suspension into said polysiloxane elastomer by crosslinking the suspending medium with the polysiloxane elastomer.

14. A medical device comprising a polysiloxane prepared according to claim 13.

15. A medical device of claim 14, wherein said device is selected from the group consisting of medical tubings and catheters.

16. A method of claim 13, wherein said antiseptic is selected from the group consisting of benzalkonium chloride, chlorhexidine, taurolidine and triclosan.

17. A silicone-rubber formulation comprising a polysiloxane component, at least one catalyst, and an antiseptic suspension, wherein, a. the polysiloxane component comprises at least one polysiloxane selected from the group consisting of:

(i) a polysiloxane according to formula (I):

(I), wherein:

$R^1$ is selected from the group consisting of: $C_1$-$C_{12}$-alkyl, $C_1$-$C_{12}$-alkenyl, $C_1$-$C_{12}$-fluoroalkyl, optionally substituted phenyl, and optionally substituted naphthyl;

$R^2$ is selected from the group consisting of: $C_1$-$C_{12}$-alkyl, $C_1$-$C_{12}$-fluoroalkyl, optionally substituted phenyl, and optionally substituted naphthyl;

wherein $R^1$ and $R^2$ may in each case be identical or different;

$R^3$ is selected from the group consisting of: $C_1$-$C_{12}$-alkyl; $C_1$-$C_{12}$-alkenyl; $C_1$-$C_{12}$-fluoroalkyl; optionally substituted phenyl; optionally substituted naphthyl;

and —OSiR$^2$R$^3$R', in which R' symbolizes the continuation of the siloxane chain of formula (I) in the branching so that the polysiloxane may have branching units of the formula $SiO_{4/2}$ and $R^3SiO_{3/2}$;

$R^4$ is selected from the group consisting of: $C_1$-$C_{12}$-alkyl, $C_1$-$C_{12}$-fluoroalkyl, optionally substituted phenyl, and optionally substituted naphthyl; and —OSiR$^2$R$^3$R', in which R' symbolizes the continuation of the siloxane chain of formula (I) in the branching so that the polysiloxane may have branching units of the formula $SiO_{4/2}$ and $R^3SiO_{3/2}$;

wherein $R^3$ and $R^4$ may in each case be identical or different, expressly including each repeating unit;

x is an integer from 2 to 15,000 and is varied so that the polysiloxane has a viscosity at 25° C. from 0.1 to 1000 Pas at 25° C.;

with the proviso that, if $R^1$ or $R^3$ is $C_1$-$C_{12}$-alkenyl, then the polysiloxane of formula I shall comprise from 0.0002 to 3% by weight of vinyl groups and at least two double bonds;

and (ii) a polyhydrosiloxane according to formula (II)

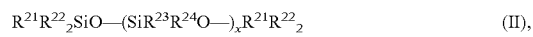
(II), wherein:

$R^{21}$ and $R^{22}$ are selected from the group consisting of $C_1$-$C_{12}$-alkyl, wherein $R^{21}$ and $R^{22}$ may in each case be identical or different, and;

$R^{23}$ in each case expressly including each repeating unit independently of one another is selected from the group consisting of: hydrogen; $C_1$-$C_{12}$-alkyl; $C_1$-$C_{12}$-fluoroalkyl; optionally substituted phenyl; optionally substituted naphthyl; and —OSiR$^{23}$R$^{24}$R" in which R" symbolizes the continuation of the siloxane chain such that the polyhydrosiloxane has branching units of the formula $SiO_{4/2}$ and $R^{23}SiO_{3/2}$, wherein $R^{23}$ in at least 4 of these silyldioxy units is hydrogen so that the polyhydrosiloxane has at least 4 crosslinking sites;

$R^{24}$ in each case expressly including each repeating unit independently of one another is selected from the group consisting of $C_1$-$C_{12}$-alkyl; $C_1$-$C_{12}$-fluoroalkyl; optionally substituted phenyl; optionally substituted naphthyl; and —OSiR$^{23}$R$^{24}$R''' in which R''' the continuation of the siloxane chain of formula (II) in the branching so that the polymer molecule has branching units of the formula $SiO_{4/2}$ and $R^{23}SiO_{3/2}$;

Y is an integer from 4 to 10,000 and is varied so that the polyhydrosiloxane has a viscosity at 25° C. from 0.0005 to 0.1 Pas;

b. the at least one catalyst comprises an element of the platinum group, where a maximum of 3 parts by weight of metal compounds such as oxides and/or carbonates, and further salts and complex compounds, of Fe, Al, Zn, Ti, Zr, Ce or other lanthanoids are present based on 100 parts by weight of component A); and c. an antiseptic suspension consisting of:

a suspending medium, at least one antiseptic, and optionally a non-functional polysiloxane, wherein:

a. said suspending medium consists of at least one polysiloxane that is chemically incorporated into the pol ysiloxane component in a crosslinking reaction, the at least one polysiloxane being selected from the group consisting of the polysiloxane according to formula (I) and the polyhydrosiloxane of the formula (II); and b. said at least one antiseptic is selected from the group consisting of bispyridinium alkanes, polymeric amidobiguanides, and quaternary ammonium compounds in an average particle size $d_{50}$ of from 0.5 to 15 µm and a particle size distribution from 0.1-30 µm.

18. A silicone-rubber formulation of claim 17 comprising at least one polysiloxane according to Formula (I) and at least one polyhydrosiloxane according to Formula (II).

19. A silicone elastomer composition comprising:
at least one silicone elastomer; and
at least one antiseptic suspension comprising:
 a suspending medium comprising at least one polysiloxane that is chemically incorporated into the at least one silicone elastomer in a crosslinking reaction,
 at least one antiseptic having an average particle size $d_{50}$ of from 0.5 to 15 µm and a particle size distribution from 0.1 to 30 µm,
 optionally a non-functional polysilozane.

20. A silicone elastomer of claim 1, wherein the $d_{50}$ of from 1 to 10 µm, and the particle distribution from 0.5 to 20 µm.

* * * * *